(12) United States Patent
Lee et al.

(10) Patent No.: US 7,897,836 B2
(45) Date of Patent: Mar. 1, 2011

(54) METHOD FOR CHANGING SEED PRODUCTIVITY OF PLANT BY CONTROLLING THE LEVEL OF ATSPF3 IN PLANT

(75) Inventors: June Seung Lee, Seoul (KR); Yoon Hi Choy, Seoul (KR); Min Jung Kim, Seoul (KR); Hong Gil Nam, Gyeongsangbuk-do (KR)

(73) Assignees: Ewha University-Industry Collaboration Foundation, Seoul (KR); Postech Academy-Industry Foundation, Gyeongsangbuk-Do (KR)

( * ) Notice: Subject to any disclaimer, the term of this patent is extended or adjusted under 35 U.S.C. 154(b) by 528 days.

(21) Appl. No.: 11/907,426

(22) Filed: Oct. 12, 2007

(65) Prior Publication Data
US 2008/0256665 A1    Oct. 16, 2008

(30) Foreign Application Priority Data
Apr. 12, 2007    (KR) .......................... 10-2007-0036202

(51) Int. Cl.
*C12N 15/82*    (2006.01)

(52) U.S. Cl. ......................................... 800/278; 800/290
(58) Field of Classification Search ........................ None
See application file for complete search history.

(56) References Cited

U.S. PATENT DOCUMENTS
7,511,190 B2 *   3/2009   Creelman et al. ............. 800/282

FOREIGN PATENT DOCUMENTS
WO    WO 2007/003409 A2 *    1/2007

* cited by examiner

*Primary Examiner* — Stuart F. Baum
(74) *Attorney, Agent, or Firm* — Buchanan Ingersoll & Rooney PC

(57) ABSTRACT

Disclosed is a method of changing the seed productivity of a plant by controlling the level of AtSPF3 in the plant. More specifically, disclosed is a method of changing the seed productivity of a plant by controlling the intracellular level of a polypeptide having the amino acid sequence represented by SEQ ID NO: 1. The AtSPF3 gene has the effect of changing the seed productivity of a plant through an increase or decrease in the expression thereof in the plant. Accordingly, the AtSPF3 gene will be useful for increasing the production of plants and breeding plants.

6 Claims, 15 Drawing Sheets

A

B

C

D

A

B

C

D

SEQUENCE LISTING

<160> NUMBER OF SEQ ID NOS: 13

<210> SEQ ID NO 1
<211> LENGTH: 568
<212> TYPE: PRT
<213> ORGANISM: Arabidopsis thaliana

<400> SEQUENCE: 1

```
Met Ala Gly Ile Asp Asn Lys Ala Ala Val Met Gly Glu Trp Phe Asp
  1               5                  10                  15

Cys Ser Thr Thr Asn His Arg Lys Arg Ser Lys Ala Glu Leu Gly Arg
             20                  25                  30

Glu Phe Ser Leu Asn Tyr Ile Lys Asn Glu Asp Ser Leu Gln Thr Thr
         35                  40                  45

Phe Gln Glu Ser Ser Arg Gly Ala Leu Arg Glu Arg Ile Ala Ala Arg
     50                  55                  60

Ser Gly Phe Asn Ala Pro Trp Leu Asn Thr Glu Asp Ile Leu Gln Ser
 65                  70                  75                  80

Lys Ser Leu Thr Ile Ser Ser Pro Gly Leu Ser Pro Ala Thr Leu Leu
                 85                  90                  95

Glu Ser Pro Val Phe Leu Ser Asn Pro Leu Leu Ser Pro Thr Thr Gly
            100                 105                 110

Lys Leu Ser Ser Val Pro Ser Asp Lys Ala Lys Ala Glu Leu Phe Asp
        115                 120                 125

Asp Ile Thr Thr Ser Leu Ala Phe Gln Thr Ile Ser Gly Ser Gly Leu
    130                 135                 140

Asp Pro Thr Asn Ile Ala Leu Glu Pro Asp Asp Ser Gln Asp Tyr Glu
145                 150                 155                 160

Glu Arg Gln Leu Gly Gly Leu Gly Asp Ser Met Ala Cys Cys Ala Pro
                165                 170                 175

Ala Asp Asp Gly Tyr Asn Trp Arg Lys Tyr Gly Gln Lys Leu Val Lys
            180                 185                 190

Gly Ser Glu Tyr Pro Arg Ser Tyr Tyr Lys Cys Thr His Pro Asn Cys
        195                 200                 205

Glu Ala Lys Lys Lys Val Glu Arg Ser Arg Glu Gly His Ile Ile Glu
    210                 215                 220

Ile Ile Tyr Thr Gly Asp His Ile His Ser Lys Pro Pro Pro Asn Arg
225                 230                 235                 240

Arg Ser Gly Ile Gly Ser Ser Gly Thr Gly Gln Asp Met Gln Ile Asp
                245                 250                 255

Ala Thr Glu Tyr Glu Gly Phe Ala Gly Thr Asn Glu Asn Ile Glu Trp
            260                 265                 270

Thr Ser Pro Val Ser Ala Glu Leu Glu Tyr Gly Ser His Ser Gly Ser
        275                 280                 285

Met Gln Val Gln Asn Gly Thr His Gln Phe Gly Tyr Gly Asp Ala Ala
    290                 295                 300
```

```
Ala Asp Ala Leu Tyr Arg Asp Glu Asn Glu Asp Asp Arg Thr Ser His
305                 310                 315                 320

Met Ser Val Ser Leu Thr Tyr Asp Gly Glu Val Glu Glu Ser Glu Ser
            325                 330                 335

Lys Arg Arg Lys Leu Glu Ala Tyr Ala Thr Glu Thr Ser Gly Ser Thr
        340                 345                 350

Arg Ala Ser Arg Glu Pro Arg Val Val Val Gln Thr Thr Ser Asp Ile
    355                 360                 365

Asp Ile Leu Asp Asp Gly Tyr Arg Trp Arg Lys Tyr Gly Gln Lys Val
370                 375                 380

Val Lys Gly Asn Pro Asn Pro Arg Ser Tyr Tyr Lys Cys Thr Ala Asn
385                 390                 395                 400

Gly Cys Thr Val Thr Lys His Val Glu Arg Ala Ser Asp Asp Phe Lys
            405                 410                 415

Ser Val Leu Thr Thr Tyr Ile Gly Lys His Thr His Val Val Pro Ala
        420                 425                 430

Ala Arg Asn Ser Ser His Val Gly Ala Gly Ser Ser Gly Thr Leu Gln
    435                 440                 445

Gly Ser Leu Ala Thr Gln Thr His Asn His Asn Val His Tyr Pro Met
450                 455                 460

Pro His Ser Arg Ser Glu Gly Leu Ala Thr Ala Asn Ser Ser Leu Phe
465                 470                 475                 480

Asp Phe Gln Ser His Leu Arg His Pro Thr Gly Phe Ser Val Tyr Ile
            485                 490                 495

Gly Gln Ser Glu Leu Ser Asp Leu Ser Met Pro Gly Leu Thr Ile Gly
        500                 505                 510

Gln Glu Lys Leu Thr Ser Leu Gln Ala Pro Asp Ile Gly Asp Pro Thr
    515                 520                 525

Gly Leu Met Leu Gln Leu Ala Ala Gln Pro Lys Val Glu Pro Val Ser
530                 535                 540

Pro Gln Gln Gly Leu Asp Leu Ser Ala Ser Ser Leu Ile Cys Arg Glu
545                 550                 555                 560

Met Leu Ser Arg Leu Arg Gln Ile
            565

<210> SEQ ID NO 2
<211> LENGTH: 1707
<212> TYPE: DNA
<213> ORGANISM: Arabidopsis thaliana

<400> SEQUENCE: 2
atggctggta ttgataataa agctgctgta atgggagaat ggttcgactg tagtactact      60
aaccacagga agagatcgaa agcggaactt ggtagagagt tttctttaaa ttacatcaag     120
aatgaggatt ctttgcaaac caccttcaa gaaagttcac gaggagctct tcgtgaaagg     180
attgctgcga gatccgggtt taatgcaccg tggttaaaca ctgaggatat tcttcagtcg     240
aaatctttaa ccatctcttc tcctggtctt agtcctgcaa ctctgttaga gtctcctgtt     300
ttcctctcaa acccttttgct atctccaaca accgggaagc tctcatcagt accttctgat     360
aaggctaaag ctgagttatt tgacgacatt ccacatcct tagccttcca aaccatttca     420
ggaagtggcc ttgatcctac taacatcgct ttagaaccg atgattccca agactatgaa     480
gaaagacagc tcggcggttt aggagactcg atggcttgtt gtgcacctgc agatgatgga     540
tacaactgga gaaaatatgg acaaaagcta gttaaggaa gtgagtatcc gcggagctat     600
```

```
tacaagtgca cgcacccgaa ttgtgaggcc aagaagaagg ttgaacggtc tcgggaaggt    660
catattatag agatcatata cacaggagat catatacaca gcaaacctcc acctaaccgc    720
cggtcaggga ttggatcatc cggtactggc aagacatgc aaatagatgc aaccgaatac    780
gaaggttttg ctggaaccaa tgagaacata gaatggacat cacctgtatc tgcagagctc    840
gaatacggaa gccattcagg atcaatgcag gttcaaaacg ggactcatca gttcgggtat    900
ggtgatgcag cagctgatgc cttatataga gatgaaaacg aagatgatcg cacgtcccac    960
atgagtgttt ccctgactta cgatggagag gtagaagagt ccgaatcaaa gagaaggaaa   1020
ctagaagctt atgcaacaga aacgagtgga tcaaccagag ccagccgtga gccaagagtt   1080
gtggtgcaga ccacaagtga cattgacatc ctcgatgatg gttatcgctg gcgcaagtat   1140
gggcaaaaag tcgttaaagg aaacccgaat ccaaggagct actataaatg cacagctaat   1200
ggatgtaccg taacgaagca tgtagagaga gcctctgatg acttcaagag cgtactaaca   1260
acttatatag gcaagcacac ccacgttgta ccagcagcac gcaacagcag ccacgtcggt   1320
gcaggcagtt cagggactct ccaaggcagt ttagcgactc agacccacaa ccacaatgtg   1380
cactatccaa tgccacacag tagatctgag ggactggcca cagccaactc atctctattt   1440
gacttccagt cacacctgag gcatcctaca ggtttctccg tttacatagg ccaatctgag   1500
ctttctgatc tttcaatgcc tggtctaact attgggcaag agaagcttac cagcctgcag   1560
gcgcctgaca ttggggatcc aactggccta atgttgcagt tagcagcaca gccgaaggtg   1620
gaaccagtgt caccacaaca gggacttgat ttgtcagcga gctcattgat atgcagagag   1680
atgttgagta gattacgaca gatatga                                        1707

<210> SEQ ID NO 3
<211> LENGTH: 327
<212> TYPE: PRT
<213> ORGANISM: Arabidopsis thaliana

<400> SEQUENCE: 3

Met Ser Asn Glu Thr Arg Asp Leu Tyr Asn Tyr Gln Tyr Pro Ser Ser
 1               5                  10                  15

Phe Ser Leu His Glu Met Met Asn Leu Pro Thr Ser Asn Pro Ser Ser
            20                  25                  30

Tyr Gly Asn Leu Pro Ser Gln Asn Gly Phe Asn Pro Ser Thr Tyr Ser
        35                  40                  45

Phe Thr Asp Cys Leu Gln Ser Ser Pro Ala Ala Tyr Glu Ser Leu Leu
    50                  55                  60

Gln Lys Thr Phe Gly Leu Ser Pro Ser Ser Ser Glu Val Phe Asn Ser
65                  70                  75                  80

Ser Ile Asp Gln Glu Pro Asn Arg Asp Val Thr Asn Asp Val Ile Asn
                85                  90                  95

Gly Gly Ala Cys Asn Glu Thr Glu Thr Arg Val Ser Pro Ser Asn Ser
            100                 105                 110

Ser Ser Ser Glu Ala Asp His Pro Gly Glu Asp Ser Gly Lys Ser Arg
        115                 120                 125

Arg Lys Arg Glu Leu Val Gly Glu Glu Asp Gln Ile Ser Lys Lys Val
    130                 135                 140

Gly Lys Thr Lys Lys Thr Glu Val Lys Lys Gln Arg Glu Pro Arg Val
145                 150                 155                 160

Ser Phe Met Thr Lys Ser Glu Val Asp His Leu Glu Asp Gly Tyr Arg
                165                 170                 175

Trp Arg Lys Tyr Gly Gln Lys Ala Val Lys Asn Ser Pro Tyr Pro Arg
```

```
                    180             185             190
Ile Ile Ala Asn Gly Asn Glu Asn Arg Ser Tyr Tyr Arg Cys Thr Thr
            195                 200             205
Gln Lys Cys Asn Val Lys Lys Arg Val Glu Arg Ser Phe Gln Asp Pro
        210             215                 220
Thr Val Val Ile Thr Thr Tyr Glu Gly Gln His Asn His Pro Ile Pro
225             230                 235                 240
Thr Asn Leu Arg Gly Ser Ser Ala Ala Ala Met Phe Ser Ala Asp
            245                 250                 255
Leu Met Thr Pro Arg Ser Phe His Asp Met Phe Arg Thr Ala Ala
            260                 265                 270
Tyr Thr Asn Gly Gly Ser Val Ala Ala Ala Leu Asp Tyr Gly Tyr Gly
            275                 280                 285
Gln Ser Gly Tyr Gly Ser Val Asn Ser Asn Pro Ser Ser His Gln Val
            290                 295                 300
Tyr His Gln Gly Gly Glu Tyr Glu Leu Leu Arg Glu Ile Phe Pro Ser
305                 310                 315                 320
Ile Phe Phe Lys Gln Glu Pro
                325

<210> SEQ ID NO 4
<211> LENGTH: 984
<212> TYPE: DNA
<213> ORGANISM: Arabidopsis thaliana

<400> SEQUENCE: 4
atgtctaatg aaaccagaga tctctacaac taccaatacc cttcatcgtt ttcgttgcac    60
gaaatgatga atctgcctac ttcaaatcca tcttcttatg aaacctccc  atcacaaaac   120
ggttttaatc catctactta ttccttcacc gattgtctcc aaagttctcc agcagcgtat   180
gaatctctac ttcagaaaac ttttggtctt tctccctctt cctcagaggt ttcaattct   240
tcgatcgatc aagaaccgaa ccgtgatgtt actaatgacg taatcaatgg tggtgcatgc   300
aacgagactg aaactagggt ttctccttct aattcttcct ctagtgaggc tgatcaccc   360
ggtgaagatt ccggtaagag ccggaggaaa cgagagttag tcggtgaaga agatcaaatt   420
tccaaaaaag ttgggaaaac gaaaaagact gaggtgaaga aacaaagaga gccacgagtc   480
tcgtttatga ctaaaagtga agttgatcat cttgaagatg gttatagatg gagaaaatac   540
ggccaaaagg ctgtaaaaaa tagcccttat ccaaggataa tagccaatgg aaacgaaaat   600
aggagttact atagatgtac aacacaaaag tgcaacgtga gaaacgagt ggagagatcg   660
ttccaagatc caacggttgt gattacaact tacgagggtc aacacaacca cccgattccg   720
actaatcttc gaggaagttc tgccgcggct gctatgttct ccgcagacct catgactcca   780
agaagctttg cacatgatat gtttaggacg gcagcttata ctaacggcgg ttctgtggcg   840
gcggctttgg attatggata tggacaaagt ggttatggta gtgtgaattc aaaccctagt   900
tctcaccaag tgtatcatca agggggtgag tatgagctct tgagggagat tttccttca   960
attttcttta agcaagagcc ttga                                         984

<210> SEQ ID NO 5
<211> LENGTH: 298
<212> TYPE: PRT
<213> ORGANISM: Arabidopsis thaliana

<400> SEQUENCE: 5

Met Ala Asp Asp Trp Asp Leu His Ala Val Val Arg Gly Cys Ser Ala
```

```
                1               5              10              15
          Val Ser Ser Ser Ala Thr Thr Val Tyr Ser Pro Gly Val Ser Ser
                         20                  25                  30

His Thr Asn Pro Ile Phe Thr Val Gly Arg Gln Ser Asn Ala Val Ser
                     35                  40                  45

Phe Gly Glu Ile Arg Asp Leu Tyr Thr Pro Phe Thr Gln Glu Ser Val
                 50                  55                  60

Val Ser Ser Phe Ser Cys Ile Asn Tyr Pro Glu Pro Arg Lys Pro
              65                  70                  75              80

Gln Asn Gln Lys Arg Pro Leu Ser Leu Ser Ala Ser Ser Gly Ser Val
                          85                  90                  95

Thr Ser Lys Pro Ser Gly Ser Asn Thr Ser Arg Ser Lys Arg Arg Lys
                         100                 105                 110

Ile Gln His Lys Lys Val Cys His Val Ala Ala Glu Ala Leu Asn Ser
                         115                 120                 125

Asp Val Trp Ala Trp Arg Lys Tyr Gly Gln Lys Pro Ile Lys Gly Ser
                     130                 135                 140

Pro Tyr Pro Arg Gly Tyr Tyr Arg Cys Ser Thr Ser Lys Gly Cys Leu
          145                 150                 155                 160

Ala Arg Lys Gln Val Glu Arg Asn Arg Ser Asp Pro Lys Met Phe Ile
                             165                 170                 175

Val Thr Tyr Thr Ala Glu His Asn His Pro Ala Pro Thr His Arg Asn
                         180                 185                 190

Ser Leu Ala Gly Ser Thr Arg Gln Lys Pro Ser Asp Gln Gln Thr Ser
                         195                 200                 205

Lys Ser Pro Thr Thr Thr Ile Ala Thr Tyr Ser Ser Pro Val Thr
                     210                 215                 220

Ser Ala Asp Glu Phe Val Leu Pro Val Glu Asp His Leu Ala Val Gly
          225                 230                 235                 240

Asp Leu Asp Gly Glu Glu Asp Leu Leu Ser Leu Ser Asp Thr Val Val
                             245                 250                 255

Ser Asp Asp Phe Phe Asp Gly Leu Glu Glu Phe Ala Ala Gly Asp Ser
                         260                 265                 270

Phe Ser Gly Asn Ser Ala Pro Ala Ser Phe Asp Leu Ser Trp Val Val
                     275                 280                 285

Asn Ser Ala Ala Thr Thr Thr Gly Gly Ile
                     290                 295

<210> SEQ ID NO 6
<211> LENGTH: 897
<212> TYPE: DNA
<213> ORGANISM: Arabidopsis thaliana

<400> SEQUENCE: 6
atggccgacg attgggatct ccacgccgta gtcagaggct gctcagccgt aagctcatca      60
gctactacca ccgtatattc ccccggcgtt tcatctcaca caaaccctat attcaccgtc     120
ggacgacaaa gtaatgccgt ctccttcgga gagattcgag atctctacac accgttcaca     180
caagaatctg tcgtctcttc gttttcttgt ataaactacc cagaagaacc tagaaagcca     240
cagaaccaga acgtcctcct ttctctctct gcttcttccg gtagcgtcac tagcaaaccc     300
agtggctcca atacctctag atctaaaaga agaaagatac agcataagaa agtgtgccat     360
gtagcagcag aagctttaaa ctccgatgtc tgggcatggc gaaagtacgg acagaaaccc     420
atcaaaggtt caccatatcc aagaggatac tacagatgta gtacatcaaa aggttgttta     480
```

-continued

```
gcccgtaaac aagtggagcg aaatagatcc gacccgaaga tgtttatcgt cacttacacg    540
gcggagcata atcatccagc tccgacacac cgtaattctc tcgccggaag cacacgtcag    600
aaaccatccg atcaacagac gagtaaatct ccgacgacca ctattgctac ttattcatcg    660
tctccggtga cttcagccga cgaatttgtt ttgcctgttg aggatcatct agcggtggga    720
gatcttgacg gagaagaaga tctgttatct ttgtcggata cggtggttag cgatgatttc    780
ttcgatgggt tagaggaatt cgcagccgga gatagctttt ccgggaactc ggctccggcg    840
agttttgatc tctcttgggt tgtgaacagt gccgccacta ccaccggagg aatatga       897
```

<210> SEQ ID NO 7
<211> LENGTH: 22
<212> TYPE: DNA
<213> ORGANISM: Artificial Sequence
<220> FEATURE:
<223> OTHER INFORMATION: primer for T-DNA left border

<400> SEQUENCE: 7

```
tggttcacgt agtgggccat cg                                              22
```

<210> SEQ ID NO 8
<211> LENGTH: 30
<212> TYPE: DNA
<213> ORGANISM: Artificial Sequence
<220> FEATURE:
<223> OTHER INFORMATION: Forward Primer for AtSPF1

<400> SEQUENCE: 8

```
atggctggta ttgataataa agctgctgta                                      30
```

<210> SEQ ID NO 9
<211> LENGTH: 30
<212> TYPE: DNA
<213> ORGANISM: Artificial Sequence
<220> FEATURE:
<223> OTHER INFORMATION: Reverse Primer for AtSPF1

<400> SEQUENCE: 9

```
tcatatctgt cgtaatctac tcaacatctc                                      30
```

<210> SEQ ID NO 10
<211> LENGTH: 30
<212> TYPE: DNA
<213> ORGANISM: Artificial Sequence
<220> FEATURE:
<223> OTHER INFORMATION: Forward Primer for AtSPF2

<400> SEQUENCE: 10

```
atgtctaatg aaaccagaga tctctacaac                                      30
```

<210> SEQ ID NO 11
<211> LENGTH: 30
<212> TYPE: DNA
<213> ORGANISM: Artificial Sequence
<220> FEATURE:
<223> OTHER INFORMATION: Reverse Primer for AtSPF2

<400> SEQUENCE: 11

```
tcaaggctct tgcttaaaga aaattgaagg                                      30
```

<210> SEQ ID NO 12
<211> LENGTH: 30
<212> TYPE: DNA
<213> ORGANISM: Artificial Sequence
<220> FEATURE:

```
<223> OTHER INFORMATION: Forward Primer for AtSPF3

<400> SEQUENCE: 12
atggccgacg attgggatct ccacgccgta                              30

<210> SEQ ID NO 13
<211> LENGTH: 30
<212> TYPE: DNA
<213> ORGANISM: Artificial Sequence
<220> FEATURE:
<223> OTHER INFORMATION: Reverse Primer for AtSPF3

<400> SEQUENCE: 13
tcatattcct ccggtggtag tggcggcact                              30
```

US 7,897,836 B2

METHOD FOR CHANGING SEED PRODUCTIVITY OF PLANT BY CONTROLLING THE LEVEL OF ATSPF3 IN PLANT

RELATED APPLICATIONS

This application claims priority to Korean patent application No. 10-2007-0036202, on filed Apr. 4, 2007, the disclosures of which are incorporated herein by reference.

FIELD OF THE INVENTION

The present invention relates to a method of changing seed productivity of plant by controlling the level of AtSPF3 in the plant, and more particularly to a method of changing the seed productivity of a plant by controlling intracellular level of a polypeptide having the amino acid sequence represented by SEQ ID NO: 1.

BACKGROUND OF THE INVENTION

Herbaceous plants have a life cycle that includes seed germination, growth and differentiation, and flowering to prepare for next generation. In such processes, interactions with various hormones as the internal growth factors as well as external environmental conditions, including light, water, temperature and soil, have important effects on the growth and differentiation of plants. The most important factor in the growth of plants is considered to be the sugars produced by the photosynthesis process, which is the most fundamental phenomenon in green plants and is an important process for obtaining an energy source, required for the survival of plant, and the structure components of plant. So, these sugars would perform an important role in the growth and development of plants throughout the life cycle of plants.

Also, the sugar can act as signaling molecule like plant hormones to control the expression of not only genes related to photosynthesis, but also genes related to metabolic and developmental processes, which are important for the growth of plants, including respiration, the synthesis and decomposition of starch and sucrose, nitrogen metabolism, cell cycle regulation, and senescence. Thus, it can be seen that sugar-related reactions in plants are linked complicatedly in view of not only metabolism, but also functions as cellular constituents and regulatory factors.

Among such sugar-related genes, SPF1 (SWEET POTATO FACTOR1) was isolated from sweet potato for the first time, and is a DNA binding protein which recognizes an SP8 motif present in the promoters of sweet potato sporamin and β-amylase genes. SPF1 is known to act as a negative regulator which inhibits the transcription of a target gene by sucrose (Ishiguro and Nakamura, 1994). SPF1 was also found in cucumber (Kim D J et al., 1997, Gene, 185: 265-269) and parsley (Rushton et al., 1996, EMBO J., 15: 5690-5700), which commonly encode a WRKY domain transcription factor.

The WRKY factor has an amino acid sequence of WRKYGQK, together with a zinc-finger-like motif at the N-terminal end. The WRKY domain has a high binding ability to a specific base sequence of (T) (T)TGAC(C/T) known as the W-box. The prior reported WRKY proteins all have one or two WRKY domains in the molecule and are classified, according to the number of the WRKY domains and the structure of zinc-finger-like motif, into three groups (Eulgem et al., 2000, Trends plant sci. 5: 199-206). To date, more than 70 WRKY genes were found in Arabidopsis thaliana, and these WRKY proteins function as transcription inducing or inhibitory factors. It was reported that the transcription of these genes is rapidly and strongly induced by wounds, pathogenic infection and non-biological stresses (Asai et al., 2002, Nature, 415: 977-983), and plays an important role in the defense mechanism of plants. Also, some WRKY genes are involved in embryogenesis, seed coat, trichome development and senescence (Miao et al., 2004, Plant Mol. Biol. 55(6): 853-867).

SUMMARY OF THE INVENTION

The present invention is based on a study on the ripening of watermelon fruits. Among ESTs obtained from the fruit flesh to screen genes related to a watermelon fruit ripening process, genes showing similarity to the SPF1-like protein homolog found in sweet potato were found. In order to examine the functions of the genes, the present inventors have indirectly studied the functions of the genes showing the similarity of sweet potato SPF1-like protein in *Arabidopsis* (AtSPF1, AtSPF2 and AtSPF3), and as a result, have found that knockout or overexpression mutants of AtSPF1 and AtSPF3 change the seed productivity of plants, thereby completing the present invention.

Accordingly, an object of the present invention is to provide a method for changing seed productivity of a plant, comprising controlling intracellular level of AtSPF3 in the plant.

Another object of the present invention is to provide a plant changed seed productivity, produced through a method comprising controlling intracellular level of AtSPF3 in the plant.

DETAILED DESCRIPTION OF THE PREFERRED EMBODIMENT

Figure 1:
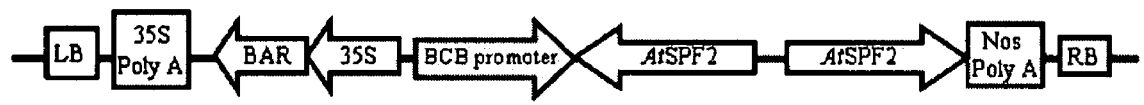
FIG. 1 is a schematic diagram showing the structures of the inventive recombinant expression vectors for AtSPF2 RNAi (A), AtSPF1 overexpression (B), AtSPF2 overexpression (C) and AtSPF3 overexpression (D) (LB: left border; 35S poly: poly A sequence for 35S promoter; BAR: Basta (phosphinothricin) resistant gene; 35S: 35S promoter; BCB promoter: *Arabidopsis thaliana* Blue Copper Binding protein promoter; Nos poly A: poly A sequence for Nos promoter; and RB: right border).
Figure 1:
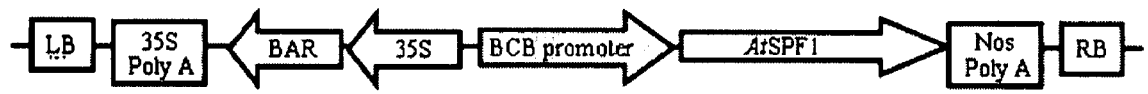
Figure 1:
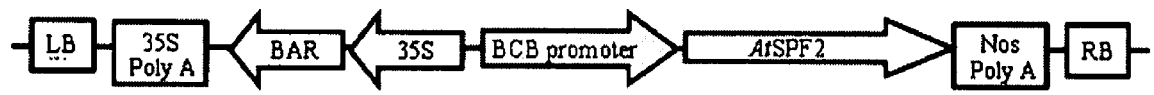
Figure 1:
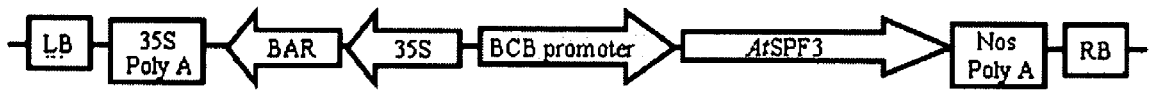

To achieve the above objects, in one aspect, the present invention provides a method for changing the seed productivity of a plant, comprising controlling the intracellular level of AtSPF3 in the plant.

In another aspect, the present invention provides a plant having changed seed productivity, produced through a method comprising controlling the cellular level of AtSPF3 in the plant.

Hereinafter, the present invention will be described in detail.

The present invention relates to a method for changing seed productivity of a plant, comprising controlling the cellular level of AtSPF3 in the plant.

AtSPF3 of the present invention is a polypeptide consisting of 298 amino acids and functions to change the seed productivity of a plant. This function of AtSPF3 was found for the first time by the present inventors. AtSPF3 is preferably the polypeptide having an amino acid sequence of SEQ ID NO: 1.

Meanwhile, the above polypeptide may be a functional equivalent to the polypeptide having the amino acid sequence represented by SEQ ID NO: 1. As used herein, the term "functional equivalents" refers to polypeptides having substantially the same physiological activity as the protein of AtSPF3, which have a sequence homology of at least 70%, and preferably at least 80%, that is, 80%, 81%, 82%, 83%, 84%, 85%, 86%, 87%, 88%, 89%, 90%, 91%, 92%, 93%, 94%, 95%, 96%, 97%, 98%, 99%, with the amino acid sequence of SEQ ID NO: 1, as a result of the addition, substitution or deletion of amino acids. As used herein, "substantially the same physiological activity" means the activity relating the seed productivity in the plant. The functional equivalents include, for example, amino acid sequence variants with substitutions, deletions or additions in some of the amino acids of the polypeptide having the amino acid sequence represented by SEQ ID NO: 1. Preferably, the substitutions of amino acid are conservative substitutions. Examples of conservative substitutions of amino acid occurring in nature are as following: Aliphatic amino acids (Gly, Ala, Pro), hydrophobic amino acids (Ile, Leu, Val), aromatic amino acids (Phe, Tyr, Trp), acidic amino acid (Asp, Glu), basic amino acids (His, Lys, Arg, Gln, Asn) and sulfur-containing amino acids (Cys, Met). The deletions of amino acids are preferably located in portions which are not involved directly in the physiological activity of AtSPF3 of the present invention. Furthermore, the scope of the functional equivalents also encompasses polypeptide derivatives having partial modifications of the chemical structure of the inventive polypeptide while maintaining the basic backbone and physiological activity of the inventive polypeptide. For example, it encompasses structural modifications for modifying the stability, storage, volatility or solubility of the inventive polypeptide and fusion protein fused with other proteins such as GFP (Green Fluorescent Protein) maintaining the physiological activity of AtSPF3 of the present invention.

As used herein, the term "seed productivity of a plant" refers to the number of seeds in one individual, and it plays an important role in the production of plants. For example, when seed productivity is increased, the production of cereals can be increased, and when seed productivity is decreased, it is possible to produce useful varieties of plants, including watermelons and melons, the seeds of which do not need to be ingested.

As used herein, the term "cellular level" refers to the amount that is present in cells, and it can be controlled using various methods known to those skilled in the art. For example, intracellular level can be controlled at the transcriptional level or the post-transcriptional level, but the scope of the present invention is not limited thereto. The controlling at the transcriptional level can be performed using known methods for increasing the expression of a gene, for example, a method of increasing the expression of a gene encoding the polypeptide of SEQ ID NO: 1 using a recombinant vector comprising the gene linked to a promoter, a method of inserting an expression regulatory sequence for increasing the expression of a gene encoding the polypeptide of SEQ ID NO: 1, around the gene, a method for inhibiting the expression of a gene, for example, a method of inducing the mutation of a promoter or gene site to inhibit promoter activity or the function of a protein, a method of expressing an antisense gene, or a method of expressing RNAi or microRNA.

As used herein, the term "promoter" means a DNA sequence which regulates the expression of a nucleic acid sequence operably linked to a specific host cell. The term "operably linked" means that one nucleic acid fragment is linked to other nucleic acid fragments, such that the function or expression thereof is influenced by the other nucleic acid fragments. In addition, the promoter may additionally comprise operator sequences for controlling transcription, sequences encoding a suitable mRNA ribosome-binding site, and sequences controlling termination of transcription or translation. As the promoter, a constitutive promoter which constitutively induces the expression of a target gene at all points of time, or an inducible promoter which induces the expression of a target gene at a specific location and point of time, can be used. For example, SV40 promoter, CMV (cytomegalovirus) promoter, CAG promoter (Hitoshi Niwa et al., Gene, 108:193-199, 1991; Monahan et al., Gene Therapy, 7:24-30, 2000), CaMV 35S promoter (Odell et al., Nature 313:810-812, 1985), Rsyn7 promoter (U.S. patent application Ser. No. 08/991,601), Rice actin promoter (McElroy et al., Plant Cell 2:163-171, 1990), Ubiquitin promoter (Christensen et al., Plant Mol. Biol. 12:619-632, 1989), and ALS promoter (U.S. patent application Ser. No. 08/409,297) may be used. In addition, promoters disclosed in U.S. Pat. Nos. 5,608,149, 5,608,144, 5,604,121, 5,569,597, 5,466,785, 5,399,680, 5,268,463 and 5,608,142 may all be used.

The controlling at the post-transcriptional level can be performed by known methods for increasing or inhibiting the expression of proteins, for example, a method of increasing or reducing the stability of mRNA transcribed from a gene encoding the polypeptide of SEQ ID NO: 1, a method of increasing or reducing the stability of a protein or a polypeptide, or a method of increasing or reducing the activity of a protein or a polypeptide.

In a specific embodiment of the above method, a target gene is transformed with a DNA sequence encoding RNA acting on transcribed RNA, such as group 1 intron RNA, M1 RNA, hammerhead RNA, hairpin RNA or micro-RNA. Alternatively, cosuppression can be induced by transformation with DNA having a same sequence or a similar sequence of a target gene.

Preferably, the control of the intracellular level of the polypeptide of SEQ ID NO: 1 can be performed by using the method of increasing or reducing the expression of a polynucleotide encoding the polypeptide. The method of increasing or reducing the expression can be performed using methods known to those skilled in the art. For example, the expression can be increased using a recombinant expression vector prepared by linking a polynucleotide encoding the polypeptide of SEQ ID NO: 1 to a promoter. Alternatively, the expression can be reduced using a recombinant expression vector prepared by linking an antisense polynucleotide for said polynucleotide to a promoter. In this regard, the polynucleotide preferably has a base sequence represented by SEQ ID NO: 2.

Examples of the plant include the angiosperm consisting of *arabidopsis*, chinese cabbage, cabbage, mustard, rape, radish, *Brassica napobrassica*, *Brassica rapa/Brassica campestris*, triticale, cauliflower, broccoli, shepherd's purse, *Cardamine flexuosa*, *Arabis glabra*, whitlow grass, *Brassica juncea*, *Brassica napus*, *Brassica oleracea*, *Brassica caulorapa*, *Brassica fimbriata*, *Brassica ruvo*, *Brassica septiceps*, *Brassica nigra*, *Cochlearia officinalis*, *Armoracia lapathifolia*, *Descurainia pinnata* and *Aubrieta deltoidea*.

In addition, the present invention provides a method for producing a plant changed seed productivity, the method comprising transforming a plant with a polynucleotide encoding AtSPF3.

The preparation of the polynucleotide for transformation can be performed using any method known to those skilled in the art, as described above.

In the present invention, the transformation of a plant with a polynucleotide encoding AtSPF3 can be performed by transformation technology known to those skilled in the art. Preferably, it can be performed using agrobacterium-mediated transformation, microprojectile bombardment, electroporation, PEG-mediated fusion, microinjection, liposome-mediated methods, In-planta transformation, Vacuum infiltration method, floral meristem dipping method, or Agrobacteria spraying method. More preferably, it can be performed using agrobacterium-mediated transformation. Herein, the polynucleotide can be operably linked to a promoter such that it can be expressed in a transformed plant. For example, it can be in the form of a recombinant expression vector operably linked to a promoter.

Standard recombinant DNA and molecular cloning techniques used herein are well known in the art and are described in Sambrook, J., Fritsch, E. F. and Maniatis, T., Molecular Cloning: A Laboratory Manual, 2nd ed., Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987)).

In one embodiment of the present invention, genes similar to the SPF1 gene were examined in *Arabidopsis thaliana* by blastx search. As a result, 11 genes similar to the SPF1 gene were identified in *Arabidopsis thaliana*, and among them, 3, genes showing the highest similarity were selected.

In another embodiment of the present invention, in order to examine the functions of the three selected genes, knockout or overexpression mutants of the genes were prepared and selected. As a result, in the case of AtSPF1 and AtSPF3 among the selected genes, knockout and overexpression mutants were easily prepared, but in the case of AtSPF2, a knockout mutant was not easily prepared. For this reason, only AtSPF1 and AtSPF3 were studied for their physiological functions.

In still another embodiment of the present invention, the wild type plant and AtSPF1 and AtSPF3 mutants were examined for their phenotype, life cycle, chlorophyll content, hypocotyl growth rate, germination rate and seed productivity. As a result, it was found that the mutants showed a clear change in seed productivity compared to the wild type.

Accordingly, the present invention provides a method of changing the seed productivity of a plant by controlling the intracellular level of AtSPF3.

The AtSPF3 gene of the present invention has the effect of changing the seed productivity of a plant through an increase or decrease in the expression thereof in the plant. Accordingly, the AtSPF3 gene of the present invention will be useful for increasing the production of plants and breeding plants.

Hereinafter, the present invention will be described in detail with reference to examples. It is to be understood, however, that these examples are illustrative only, and the scope of the present invention is not limited thereto.

EXAMPLES

Example 1

Investigation of Genes Similar to SPF1 Gene in *Arabidopsis thaliana*

<1-1> Investigation of AtSPF1 and AtSPF3 Genes

Genes similar to the SPF1-like protein homolog, found in the watermelon fruit flesh through the previous experiment, were investigated in *Arabidopsis thaliana*. Through blastx search in the NCBI website it was seen that 11 genes similar to the SPF1 (NCBI Accession No. D30038) found in sweet potato are present in *Arabidopsis thaliana*. Among the 11 genes, three genes showing the highest similarity to the sweet potato SPF1 gene were selected. The selected genes were named AtSPF1 (At4g26440), AtSPF2 (At4g18170), and AtSPF3 (At4g01250).

It was found that the AtSPF1 gene was 1,955 bp in size and consisted of 4 exons, in which one WRKY domain was present in the $2^{nd}$ exon, and one WRKY domain was present over the $3^{rd}$ and $4^{th}$ exons. The AtSPF2 gene is 1,184 bp in size and consisted of three exons, in which one WRKY domain was present over the $2^{nd}$ and $3^{rd}$ exons. The AtSPF3 gene was 1,291 bp in size and consisted of three exons, in which one WRKY domain was present over the $2^{nd}$ and $3^{rd}$ exons.

Example 2

Studies on Functions of AtSPF Genes

<2-1> Preparation of Knockout Mutants of AtSPF Genes

In order to examine the genes, the seeds of AtSPF knockout mutants were obtained from ABRC (Arabidopsis Biological Resource Center). For AtSPF1, the mutant 1 line (SALK133019, FIG. 7A-(a)) could be secured, and for AtSPF3, the mutant 2 line (SALK094892; SALK098205, FIG. 9A) could be secured. However, for the AtSPF2 gene, an AtSPF2-RNAi transgenic plant was constructed using an RNAi technique in the following manner (see FIG. 1A) because a T-DNA insertion mutant is not yet reported.

Into a pBS-int vector (provided from Dr. Nam-Hai. Chua; a vector in which the $3^{rd}$ exon of Actin12 is inserted between the HindIII and EcoRI restriction enzyme sites of a pBluescript vector) prepared by inserting a 155-bp Act12-$3^{rd}$ intron into MCS (multi cloning site) of pBluscriptII KS (Stratagene, USA), the ORF (open reading frame) of the AtSPF2 gene was inserted in the anti-sense and sense directions while interposing the intron therebetween. In this regard, the insertion of the pBS-int vector in the sense direction was performed at the Not I restriction enzyme site of the pBS-int vector, and the insertion in the antisense direction was performed at the Apa I and Sal I restriction enzyme sites). The resulting vector was inserted into a p3301:BCB vector obtained by removing a GUS portion together with a 35S promoter from a pCAMBIA 3301 vector (Cambia, USA) and newly inserting a BCB promoter into the 3301 vector. The p3301:BCB vector was prepared in the following manner: the pCAMBIA 3301 was treated with Hind III and treated with a Klenow enzyme to make a blunt end. Then, the vector was treated with PmlI to remove 2480 bp ranging from lacZ alpha to histidine tag. The vector was self-ligated, and then a sequence ranging from the 1573-bp upstream of BCB protein (Blue Copper Binding protein (CA78771) to ATG was inserted into the EcoRI restriction enzyme site of the self-ligated vector. The p3301: BCB vector was treated with SmaI, and then the AtSPF2 antisense ORF-intron-AtSPF2 sense ORF portion inserted into the pBS-int vector was cut with BSSHI, treated with a Klenow enzyme to make a blunt end, and then ligated with the p3301:BCB vector. Then, the vector was transformed using the agrobacterium-mediated floral dipping method (Plant J. 16: 735-743, 1998) into *Arabidopsis thaliana*, which was grown under a long-day condition at 23±1° C. for 3-4 weeks to a flower stalk length of 2-10 cm, thus obtaining the transformants.

<2-2> Preparation of Overexpression Mutants of AtSPF Genes

In order to construct overexpression mutants of AtSPF genes, the genes were expressed in Arabidopsis thaliana under the control of blue copper binding protein (BCB), the expression of which is increased by Methyl Jasmonate and various environmental stresses (see FIGS. 1B to 1D).

After the ORF portions of AtSPF1, AtSPF2 and AtSPF3 were obtained, each of the ORF portions were treated with T4 DNA polymerase to make the blunt ends. Each of the genes was inserted into the SmaI restriction enzyme site of the p3301:BCB vector to construct a binary vector, which could be transformed into a plant. The binary vector was transformed into *Arabidopsis thaliana*, which was grown under a long-day condition at 23±1° C. for 3-4 weeks to a flower stalk length of 2-10 cm, using the agrobacterium-mediated floral dipping method, thus obtaining transformants.

<2-3> Selection of Mutants

In order to germinate the dispensed knockout mutant seeds and select the homozygote line of each gene, the seeds were grown in a 0.5×MS medium (Murashige & Skoog) containing 1% sucrose and 35 µg/L kanamycin resistant antibiotic) for 3 weeks, and then the kanamycin-resistant plants were transferred into bed soil (Sunshine Mix #5, SUN GRO; hereinafter, bed soil was used in pot cultivation) and grown in a constant temperature room at 23±1° C. under a 16-hr light/8-hr dark cycle, thus obtaining seeds for each individual.

The obtained seeds were grown in a 0.5×MS medium (containing 1% sucrose) for 2 weeks, and then genomic DNA was isolated from the plants using the Dellaporta plant DNA extraction method (Dellaporata et al., Plant Mol Biol Rep 1:19-21, 1983). T-DNA insertion and the homozygote line were confirmed through PCR in the following manner.

Figure 2:
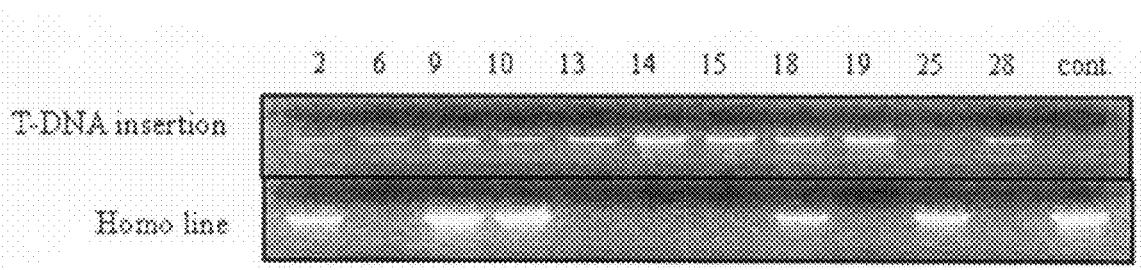
FIG. 2 shows the results of screening of homozygotes from the inventive AtSPF1 knockout mutants (A) and AtSPF3 knockout mutants (B).
Figure 2:
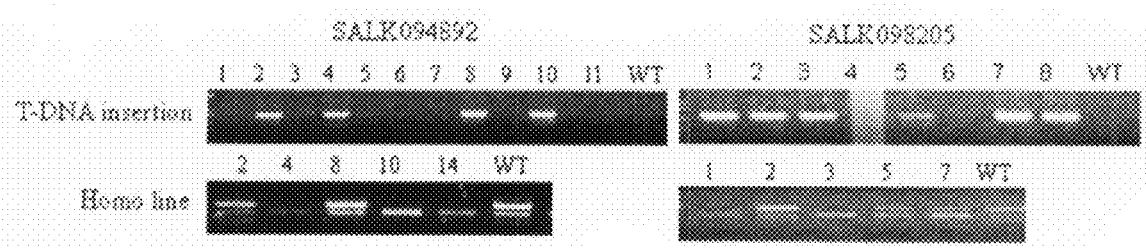

For AtSPF1, in order to confirm T-DNA insertion, PCR was performed using a primer of SEQ ID NO: 7 (corresponding to the left board of T-DNA; TGGTTCACGTAGTGGGC-CATCG) and a primer of SEQ ID NO: 9 (AtSPF1 R: TCATATCTGTCGTAATCTACTCAACATCTC), and then lines showing about 1.9-kbp PCR products having T-DNA inserted therein were selected. In order to examine whether the ORF of the AtSPF1 gene was present on the selected line, PCR was performed again using a primer of SEQ ID NO: 8 (AtSPF1 F: ATGGCTGGTATTGATAATAAAGCTGCT-GTA) and a primer of SEQ ID NO: 9 (AtSPF1 R), and a line showing no amplification of the PCR products was selected as the homozygote line (see FIG. 2A).

For AtSPF3, in order to confirm T-DNA insertion in the same manner as described above, PCR was performed using a primer of SEQ ID NO: 7 (corresponding to the left board of T-DNA; TGGTTCACGTAGTGGGCCATCG) and a primer of SEQ ID NO: 13 (AtSPF3 R: TCATATTCCTCCGGTGG-TAGTGGCGGCACT), and lines showing about 700-bp PCR products having T-DNA inserted therein were selected. In order to examine whether the ORF of the AtSPF3 gene was present on the selected lines, PCR was performed using a primer of SEQ ID NO: 12 (AtSPF3 F: ATGGCCGACGAT-TGGGATCTCCACGCCGTA) and a primer of SEQ ID NO: 13 (AtSPF3 R), and a line showing no amplification of the PCR products was selected as the homozygote line (see FIG. 2B).

For the AtSPF2 RNAi mutant and the AtSPF1, AtSPF2 and AtSPF3 overexpression mutants, the T1 seeds were sown in bed soil, and 0.01% basta was periodically sprayed in order to select basta-resistant plants, thus obtaining T2 seeds for each individual. The obtained T2 seeds were sown in 0.5×MS media (containing 1% sucrose and 50 µg/L of PPT (DL-phosphinothricin)) in a density of 200 seeds per medium, and lines showing a ratio of number of basta-resistant individuals: number of basta-sensitive individuals of 3:1 were selected (p-value>0.05 by statistical analysis with Chi-square ($X^2$) goodness of fit test) and regarded to have one copy of T-DNA inserted therein (see Table 2). The individuals thus selected were sown and cultivated to obtain seeds individually. The obtained seeds were sown in 0.5×MS media (containing 1% sucrose medium and 50 µg/L of PPT (DL-phosphinothricin)), and lines showing all-basta resistance in the next generation (T3) were selected as homozygote lines (see Table 1).

TABLE 1

| | | Measured value | | Expected value | | | |
|---|---|---|---|---|---|---|---|
| | | Basta$^R$ | Basta$^S$ | Basta$^R$ | Basta$^S$ | $X^2$ | P value |
| AtSPF1 | #9 | 152 | 64 | 162 | 54 | 2.47 | P > 0.05 |
| overex- | #15 | 193 | 59 | 189 | 63 | 0.34 | P > 0.05 |
| pression | #17 | 160 | 44 | 153 | 51 | 1.28 | P > 0.05 |
| plant | #18 | 135 | 55 | 142.5 | 47.5 | 1.58 | P > 0.05 |
| AtSPF2 | #7 | 120 | 49 | 126.75 | 42.25 | 1.44 | P > 0.05 |
| knock- | #10 | 169 | 46 | 161.25 | 53.75 | 1.49 | P > 0.05 |
| out | #11 | 159 | 59 | 163.5 | 54.5 | 0.50 | P > 0.05 |
| plant | #13 | 173 | 63 | 177 | 59 | 0.36 | P > 0.05 |
| | #16 | 151 | 67 | 163.5 | 54.5 | 3.82 | P > 0.05 |
| AtSPF2 | #3 | 206 | 52 | 193.5 | 64.5 | 3.23 | P > 0.05 |
| overex- | #11 | 128 | 42 | 127.5 | 42.5 | 0.01 | P > 0.05 |
| pression plant | | | | | | | |
| AtSPF3 | #11 | 146 | 37 | 137.25 | 45.75 | 2.23 | P > 0.05 |
| overex- | #12 | 179 | 67 | 184.5 | 61.5 | 0.66 | P > 0.05 |
| pression | #14 | 125 | 52 | 132.75 | 44.25 | 1.81 | P > 0.05 |
| plant | #18 | 175 | 56 | 173.25 | 57.75 | 0.07 | P > 0.05 |

(Basta$^R$: basta resistant; Basta$^S$: basta sensitive)

<2-4> Examination of Expression of Gene in Homozygote Lines

Three lines for each of the knockout mutants and the overexpression mutants, screened using the homozygote lines, were selected and grown in 0.5×MS media (containing 1% sucrose) for 2 weeks. Then, total RNA was isolated from the plants, and the expression level of each was examined by Northern blot analysis and RT-PCR.

The isolation of total RNA was performed using a TRI reagent (MRC, USA) according to the manufacturer's guideline. 10 µg of RNA was developed by electrophoresis on 1.2% agarose gel containing 5.5% formaldehyde, and then was transferred to a Hybond-N+ nylon membrane (Amersham Bioscience, USA) using a capillary transfer method. Then, the RNA was hybridized with a probe for each of the AtSPF1, AtSPF2 and AtSPF3 genes.

RT-PCR was performed in a total volume of 20 µl containing 2 µg of total RNA, 25 ng of an oligo(dT)$_{15}$ primer, 10 mM of dNTP mixture, 2 µl of 10× reaction buffer, 5 mM of MgCl$_2$, 2 units of a ribonuclease inhibitor and 15 units of AMV reverse transcriptase (Promega, USA) at 42° C. for 60 minutes and then 95° C. for 5 minutes, thus synthesizing cDNA. PCR was performed using the synthesized cDNA as a template with primers of SEQ ID NO: 8 and SEQ ID NO: 9 for AtSPF1, primers of SEQ ID NO: 10(AtSPF2 F: ATGTCTAATGAAACCAGAGATCTCTACAAC) and SEQ ID NO: 11 (AtSPF2 R: TCAAGGCTCTTGCTTAAA-GAAAATTGAAGG) for AtSPF2 and primers of SEQ ID NO: 12 and SEQ ID NO: 13 for AtSPF3. Also, the PCR was performed for 30 cycles of 30 sec at 94° C., 30 sec at 52° C. and 1 min at 72° C.

Figure 3:
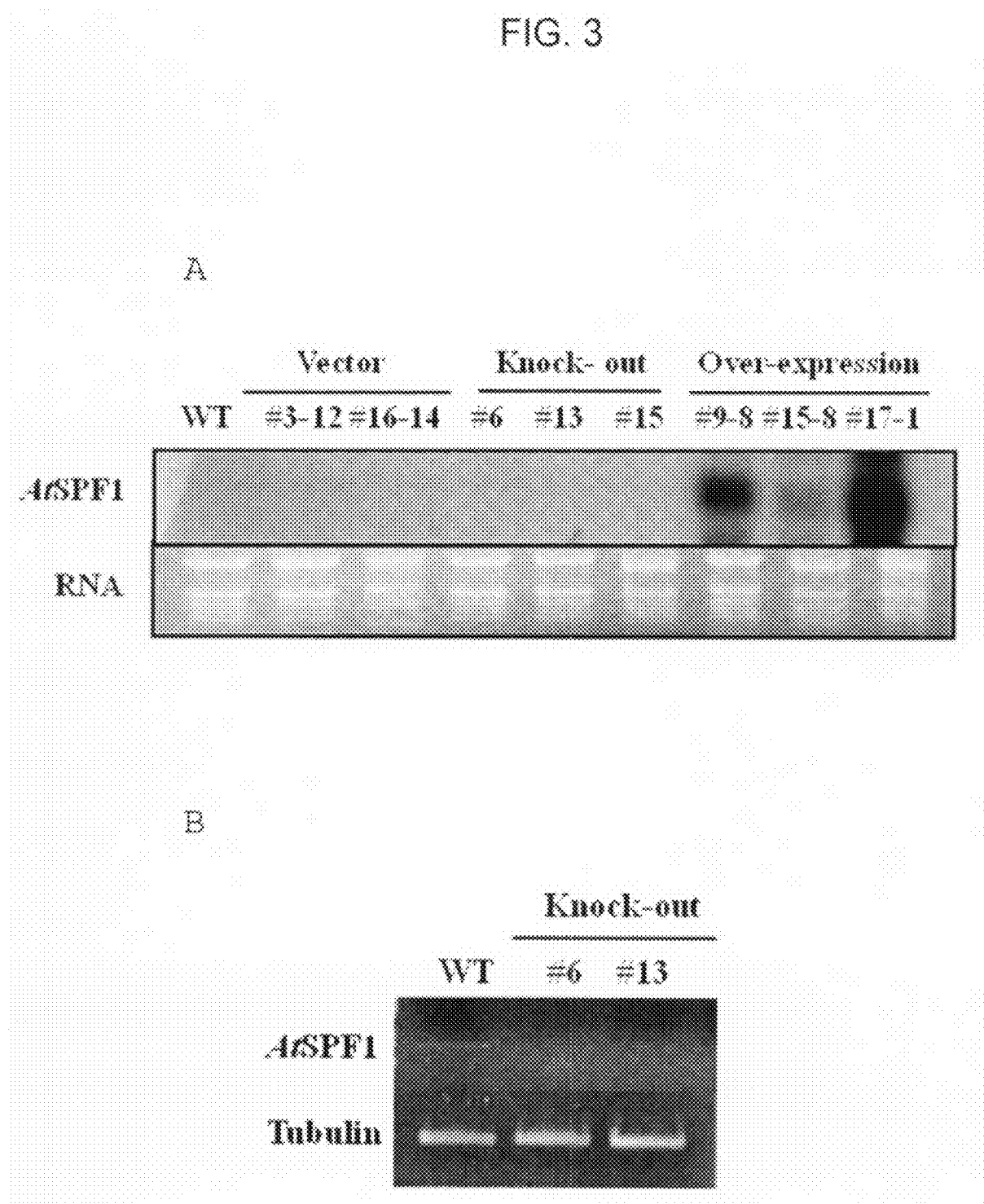
FIG. 3 shows the expression or non-expression of AtSPF1, AtSPF2 and AtSPF3 in the inventive AtSPF1 mutants (A and B), AtSPF2 mutants (C and D) and AtSPF3 mutants (E), respectively.
Figure 3:
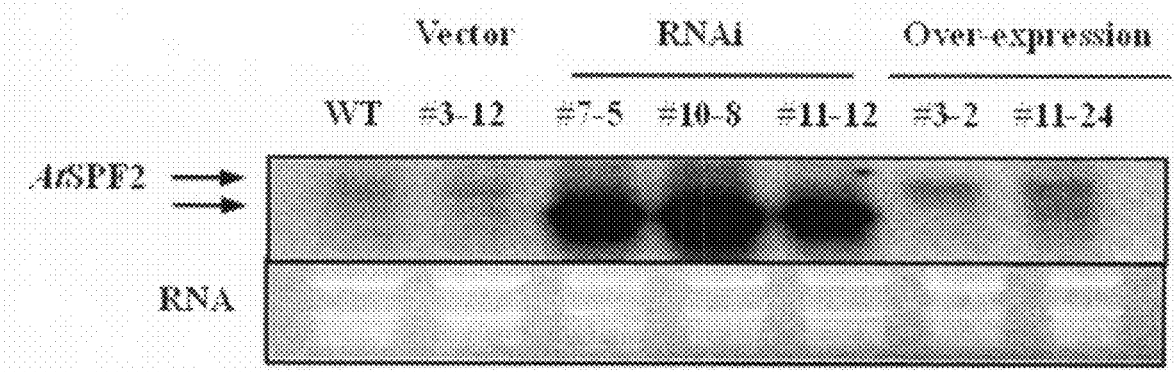
Figure 3:
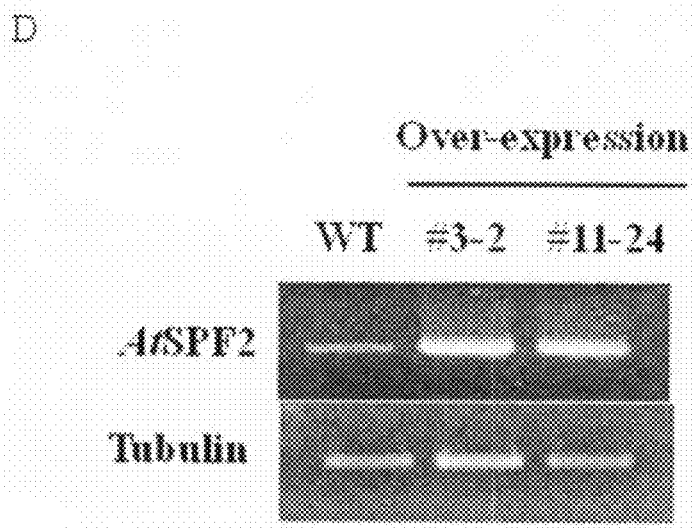
Figure 3:
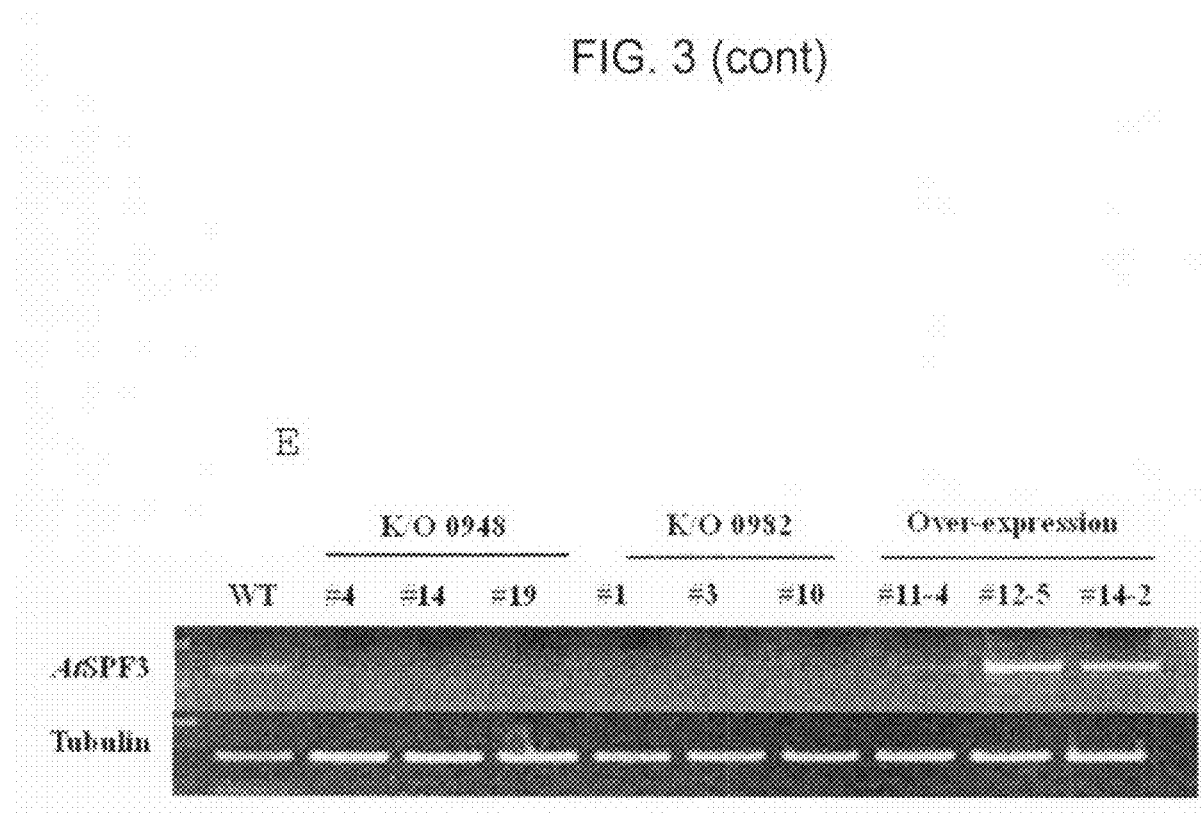

As a result, as can be seen in FIG. 3, the expression of the AtSPF1 gene in the overexpression mutant was markedly increased (FIG. 3A). However, whether the expression of the gene in the knockout mutant would be inhibited could not be confirmed, because the expression of the gene in a wild type as a control group was not confirmed. For this reason, the expression of the gene was analyzed by performing RT-PCR for the wild type and the knockout mutant which are grown in bed soil for 5 weeks as described above. As a result, it could be seen that AtSPF1 was expressed in the wild type, whereas it was not expressed in the knock out mutant line (see FIG. 3B).

In the case of AtSPF2, it could be observed that the expression of the gene in the overexpression mutant showed a tendency to increase compared to the wild type, and this tendency could also be confirmed in RT-PCR. However, in the case of the knockout transformant with RNAi, the expression of the gene was not reduced, and a band having a slightly smaller size than the original size of the gene was overexpressed, suggesting that the expression of the AtSPF2 gene was not inhibited (see FIGS. 3C and 3D).

In the case of AtSPF3, it could be observed that the expression of the gene was inhibited in the knockout mutants (K/O 0948 (SALK094892) and K/O 0982 (SALK098205)) and increased in the overexpression mutant (see 3E).

Through the preparation and verification of the transformants, for AtSPF1, #6 and #13 were selected as the knockout mutants, and #9-8 and #17-1 were selected as the overexpression mutants. For AtSPF3, K/00948 #4 and K/00982 #1 were selected as the knockout mutants, and #12-5 and #14-2 were selected as the overexpression mutants. The selected mutants were used in the following experiment to examine the functions of AtSPF1 and AtSPF3.

Example 3

Change in Physiological Activity of AtSPF1 Mutants

<3-1> Comparison of Phenotype Between Mutants and Wild Type

The knockout mutants and overexpression mutants of the AtSPF1 gene, together with the wild type, were planted and grown in the same pot for 3-5 weeks, and then the phenotypes thereof were compared.

Figure 4:
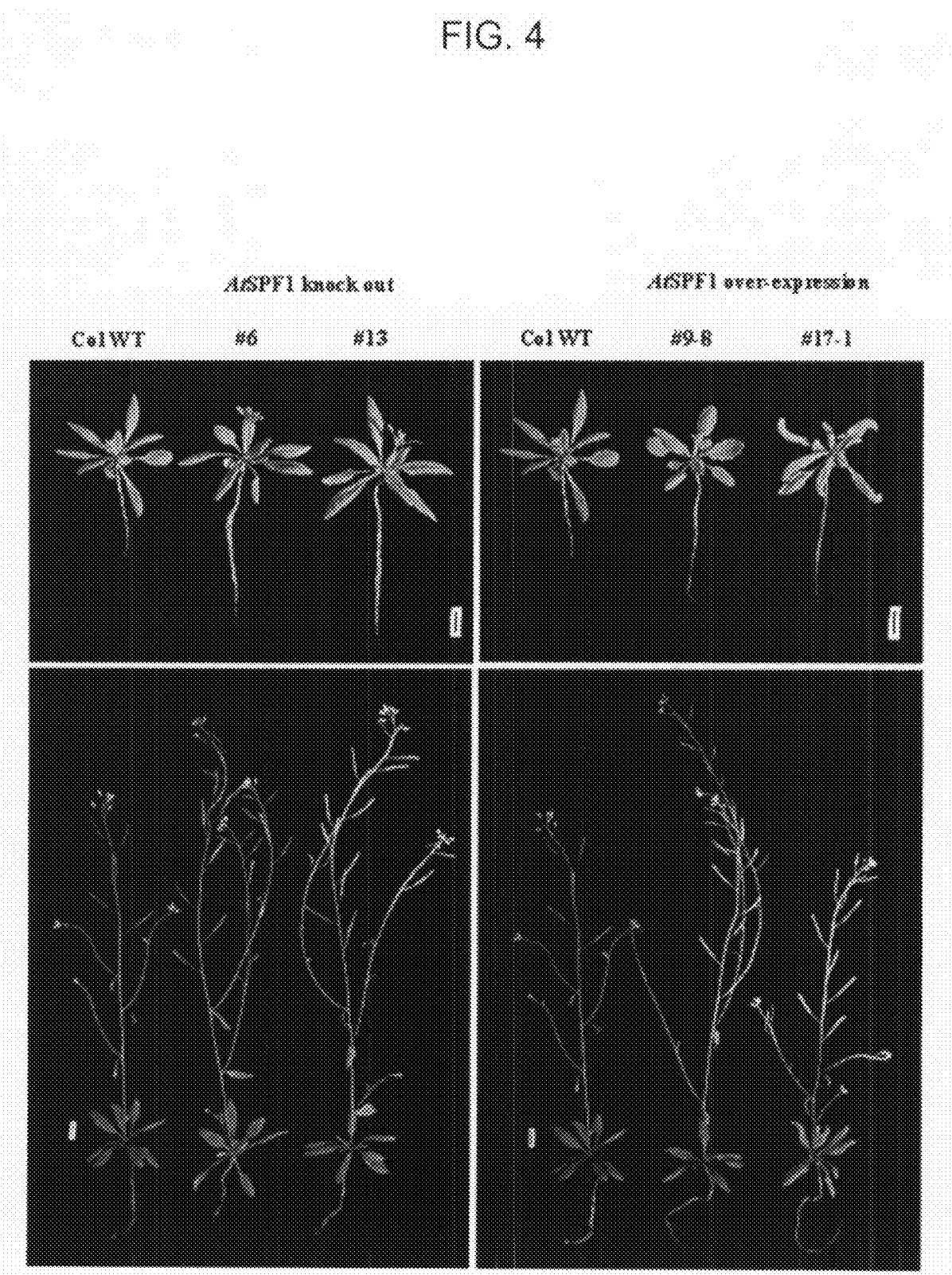
FIG. 4 shows the comparison of phenotype between the inventive AtSPF1 mutants and the wild type.

As a result, as shown in FIG. 4, in the knockout mutant line in which the expression of the AtSPF1 gene has been inhibited, the phenotype was not clearly different from the wild type. However, in the overexpression mutant #17-1 in which the gene has been expressed at the highest level, it could be observed that the color of leaves in the 4-week-old plant, immediately before the flower stalk came up, became light compared to that in the wild type, and the leaves were curled backward. Also, in the senescence stage, in which the flower stalk came up and the seeds were formed, the mutant #17-1 had a height similar to that of the wild type, but the formation of pods was slightly reduced.

<3-2> Comparison of Life Cycle Between Mutants and Wild Type

Because the AtSPF genes have similarity to sweet potato SPF1 found to be sugar-related genes, and sugars play an important role in the growth of plants, in planta assay was performed using transformants of the AtSPF genes in the following manner in order to examine the effects of expression of the genes on the development and life cycle of plants. The wild type, the AtSPF1 knockout and the overexpression mutants were planted and growth in the same pot in order to maintain conditions required for the growth of the plants at the same conditions, and each individual was observed for germination, emergence (formation of $3^{rd}$-$4^{th}$ leaves), bolting, and senescence initiation (senescence of leaves 3-4), and 50% senescence (senescence of 50% of leaf area). The observation was repeated three times in a batch of two pots.

Figure 5:
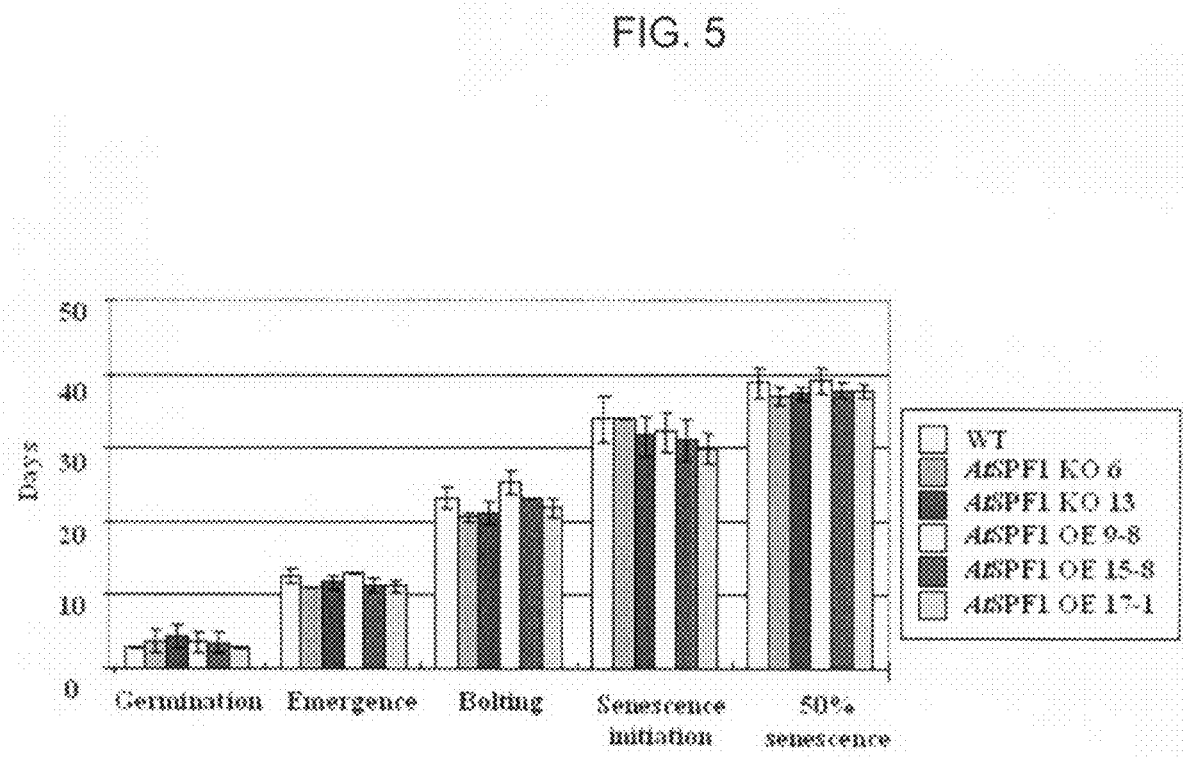
FIG. 5 shows the comparison of life cycles between the inventive AtSPF1 mutants and the wild type. (KO: knockout mutant; and OE: overexpression mutant).

As a result, as shown in FIG. 5, the bolting of the AtSPF1 gene knockout mutant occurred slightly faster, but there was no great difference from the wild type in the progression of senescence, including germination.

<3-3> Comparison of Chlorophyll Content

In Example <3-1>, it could be observed that the color of leaves in the AtSPF1 gene overexpression mutants became light compared to that in the wild type. In order to confirm whether this difference in leaf color was attributable to the difference in the content of chlorophyll in the leaves, the content of chlorophyll in $3^{rd}$-$4^{th}$ leaves grown in bed soil for 4 weeks was measured.

The $3^{rd}$-$4^{th}$ leaves of the plants grown in bed soil for 4 weeks were floated in Mes-Tris buffer (5 mM, pH 6.5) in a manner such that the backside faced upward. Then, the leaves were subjected to dark treatment at a temperature of 23±1° C. for 0 day, 1 day, 2 days and 3 days. In order to extract chlorophyll, 95% ethanol was added to the leaves in an amount of 500 µl per two leaves, and the solution was heated at 80° C. Then, the OD value of the solution excluding the leaves was measured at 648 nm and 664 nm. Based on the measured OD value, the amount of chlorophyll was calculated according to the following equation (Lichtenthaler, H. K. Methods in enzymol. 148:350-382, 1987):

{(OD value measured at 648 nm×22.24)+(OD value measured at 664 nm×5.24)}/ethanol volume/ number of leaves Also, because the color of the leaves was pale-green compared to that of the wild type, and the progression of senescence was promoted in environmental conditions inducing senescence, the leaves were floated in 5 mM Mes-Tris buffer (pH 6.5) in a manner such that the pores of the leaf backside were brought into contact with air. The floated leaves were subjected to dark treatment for 3 days, and the change in the chlorophyll content of the leaves was compared with that of the wild type.

Figure 6:
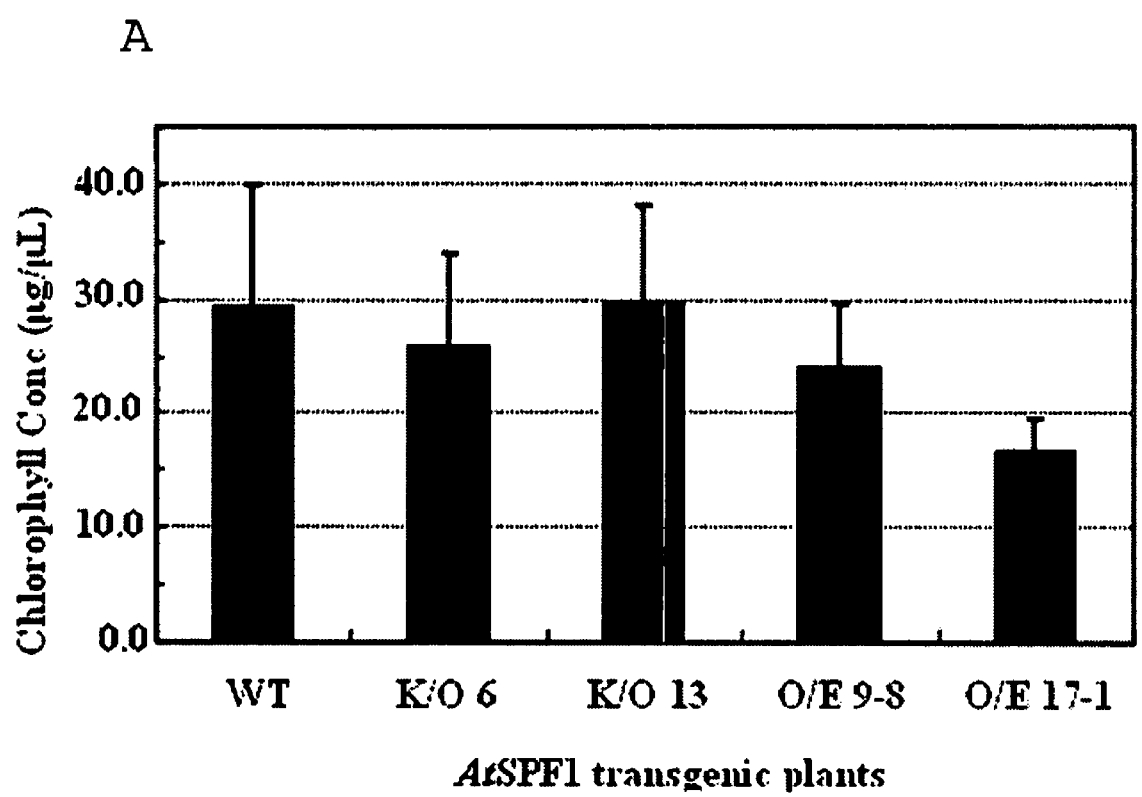
FIG. 6 shows the comparison of chlorophyll content (A) between the inventive AtSPF1 mutants and the wild type and the comparison of chlorophyll content when senescence is accelerated by dark stress (B). (K/O: knockout mutant; and O/E: overexpression mutant).
Figure 6:
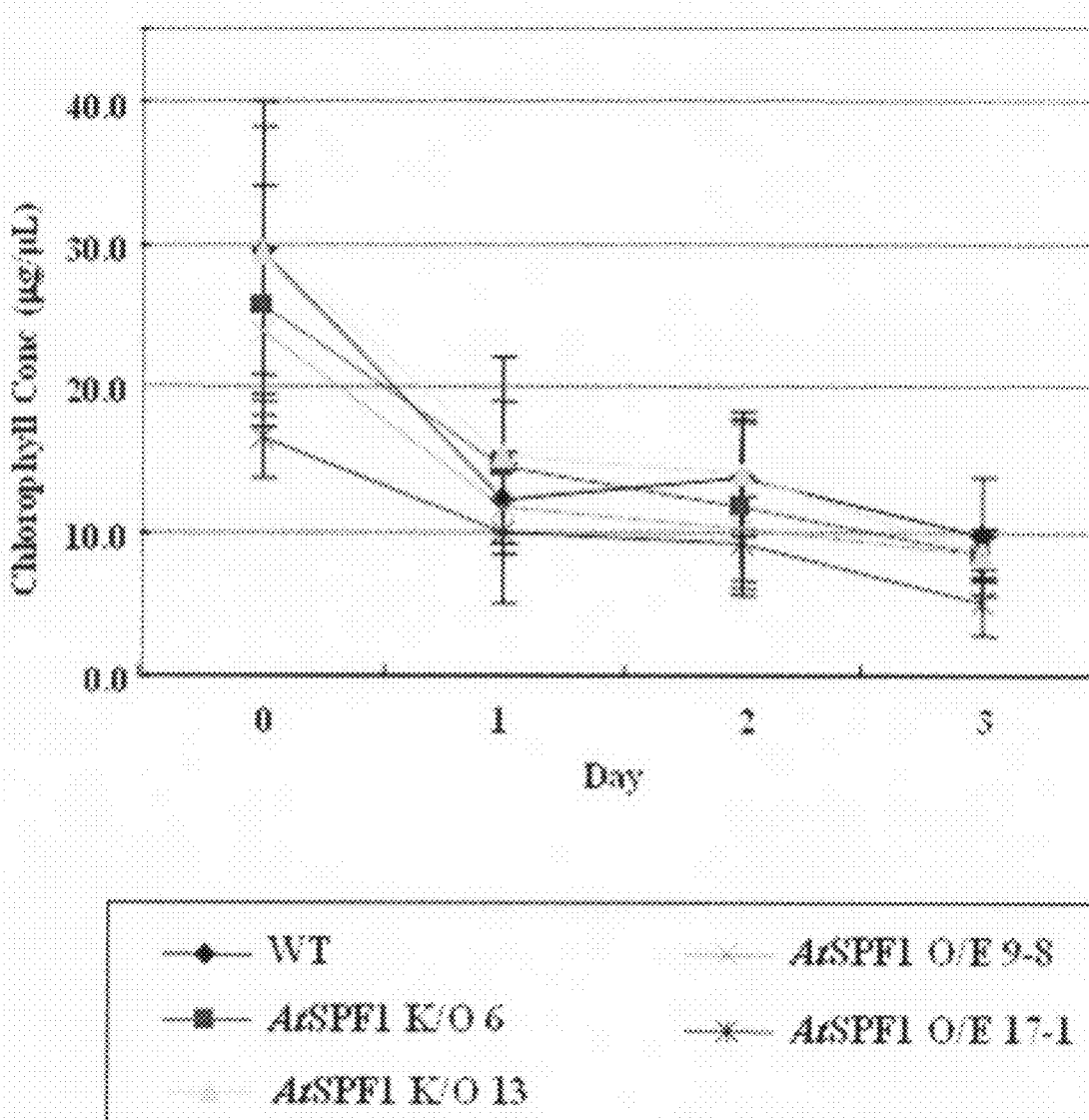

As a result, as shown in FIG. 6, the AtSPF1 overexpression mutant #17-1, which have shown a phenotype of pale-green leaf color, had a chlorophyll content lower than that of the wild type by about 43.6%, but the chlorophyll content of the overexpression mutant #9-8 or mutants inhibited AtSPF1 expression was similar to that of the wild type or was decreased by about 13% compared to that of the wild type (FIG. 6A). From this, it could be supposed that the production of chlorophyll would be markedly reduced, when the expression of the gene would be increased to a given level or higher. However, the leaves were subjected to dark treatment for 3 days to induce the degradation of chlorophyll, and then the chlorophyll content of the leaves was compared with the chlorophyll content before the dark treatment. As a result, the chlorophyll content of the AtSPF1 transformants was reduced in a rate similar to that of the wild type, suggesting that the chlorophyll content of the transformants was not influenced by natural conditions or senescence-promoting conditions (see FIG. 6B).

<3-4> Change in Hypocotyl Growth Rate

In order to examine the influence of the AtSPF gene on the growth of plants, the length of hypocotyls was measured. For this purpose, the transformant seeds together with the wild type were sown in 0.5×MS media (containing 0%, 1%, 3% and 5% sucrose) and subjected to light treatment for 12 hours. Also, in order to exclude the influence of sugars photosynthesized in seed leaves upon germination, the seeds were subjected to dark treatment for 3.5 days to induce germination. After completion of the dark treatment, the length of the plant, excluding the seed leaves and the roots, was measured. The transformant seeds and the wild type seeds were sown at a density of 30 seeds per medium, and the experiment was repeated two times or more in a set of three media.

Figure 7:
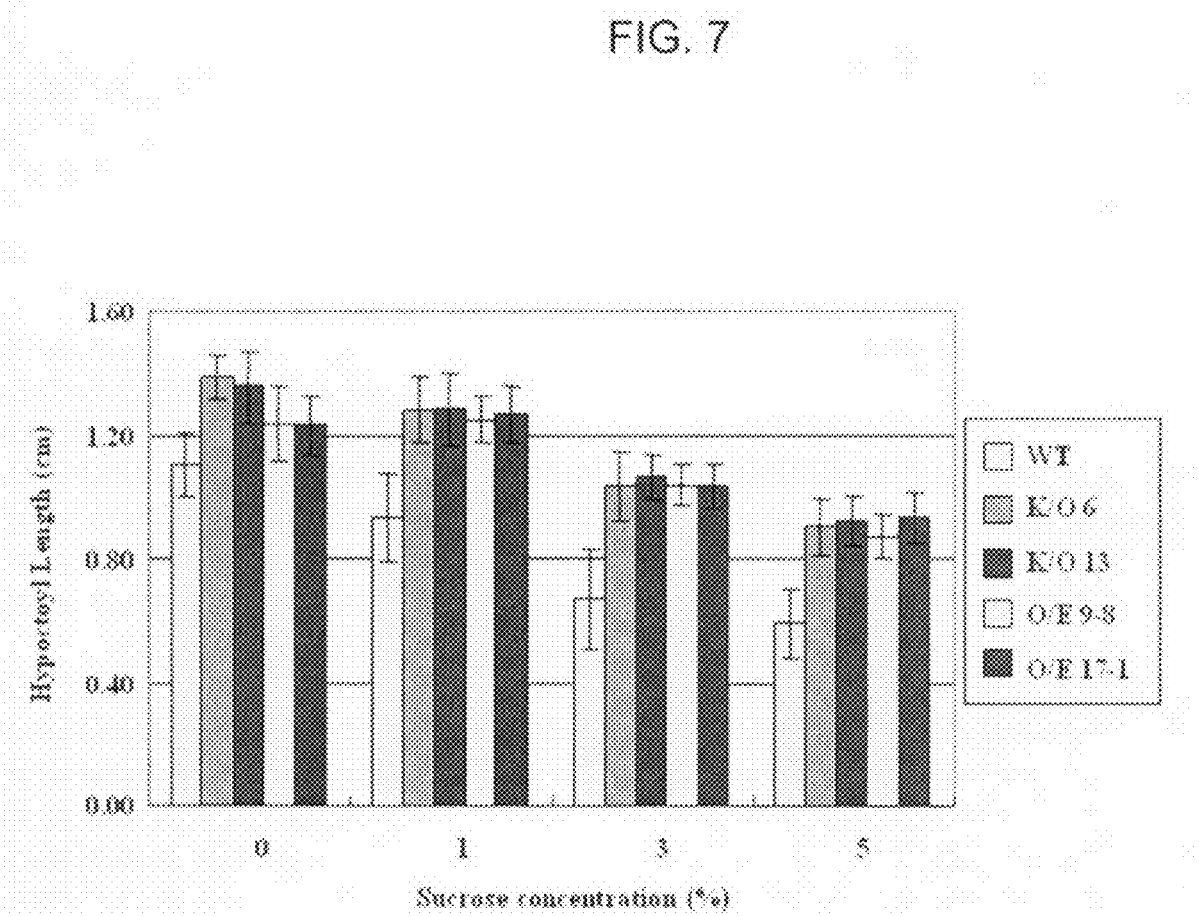
FIG. 7 shows the comparison of hypocotyl growth rate between the inventive AtSPF1 mutants and the wild type in presence of some sucrose concentration.

As a result, as shown in FIG. 7, the hypocotyl length of the transformants was longer than that of the wild type regardless of the concentration of sucrose or the expression level of the gene, and the AtSPF1 overexpression mutant #17-1, which showed the change in leaf color, also showed the same result.

<3-5> Change in Germination Rate

During the process of measuring the length of hypocotyls in order to examine the association with the growth of the plants, it could be observed that the germination rate of the transformants was higher than that of the wild type. Thus, in order to examine the influence of treatment with various stresses, including sugars, on the germination rate of the transformants, the following test was carried out.

The transformants of the respective genes, together with the wild type, were sown in 0.5×MS media (containing each of 0, 50, 100 and 200 mM NaCl, each of 0, 0.1, 0.5, 1, 5 and 10 μM ABA, each of 0, 1, 3 and 5% sucrose and each of 0, 1, 3, 5, 7 and 10% mannitol) and subjected to light treatment at 23±1° C. for 12 hours and dark treatment for 3.5 days. When the seed leaves were formed, the germination rate of the plants was measured. The transformant seeds and the wild type seeds were sown at a density of 30 seeds per medium, and the experiment was repeated two times or more in a set of three media.

Figure 8:
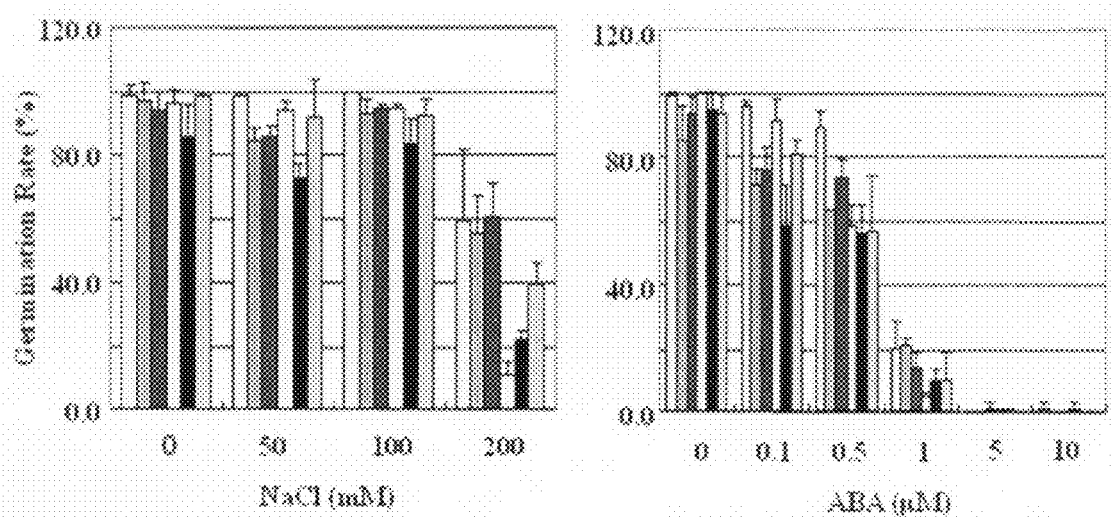
FIG. 8 shows the comparison of germination rate between the inventive AtSPF1 mutants and the wild type under the various kinds of water stress.
Figure 8:
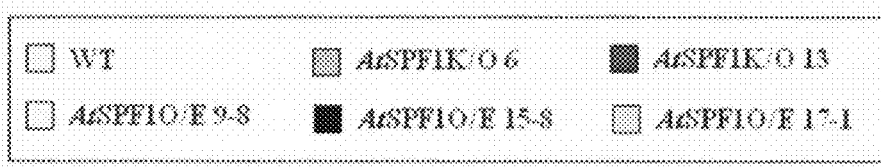
Figure 8:
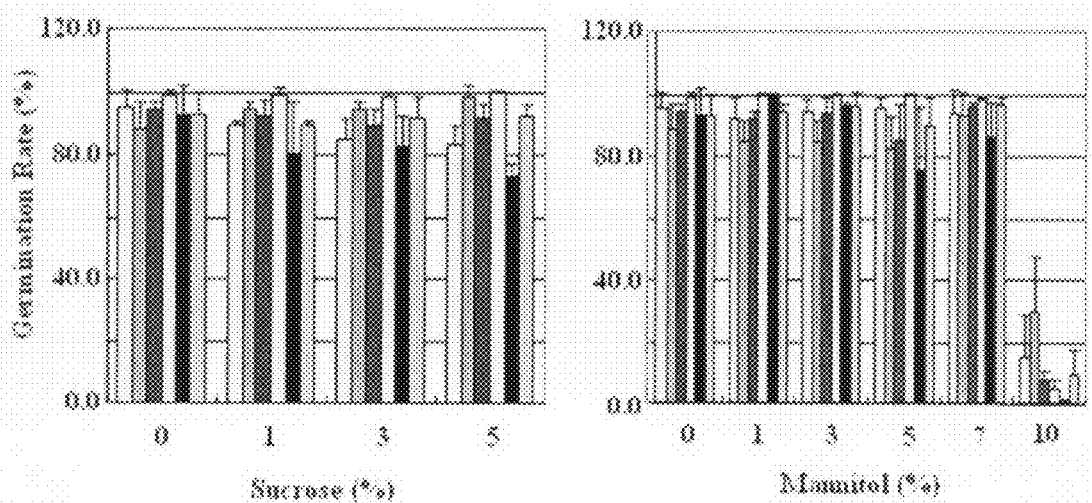

As a result, as shown in FIG. 8, the AtSPF1 gene transformants showed a germination rate slightly higher than that of the wild type in treatment with a high concentration of sucrose, but the change in germination rate with the change in the expression of the gene could not be observed. Also, the effect of osmotic stress caused by mannitol was examined, and as a result, special events were not shown. However, when the transformants were treated with salt stress (NaCl) and ABA, which is a germination inhibitory hormone, the germination rate of the AtSPF1 overexpression mutant was clearly reduced.

<3-6> Change in Seed Productivity

The growth of plants in the case of the AtSPF1 gene transformants showed a tendency to be promoted, and the overexpression of the gene led to the morphological change of leaves. Thus, in order to examine the influence of these changes on seed productivity, the seed productivity of each transformant was measured.

The transformant of each gene and the wild type were sown in the same pot and grown at 23±1° C. for 2 months under a long-day condition. The number of pods formed per individual in 10 individuals for each of the transformants and the wild type was recorded, 10 pods per individual were random selected, and the number of seeds produced per pod was recorded. On the basis of the recorded values, the seed productivity was calculated. The experiment was repeated 3 times in a batch of two pots.

As a result, as shown in Table 2 below, the AtSPF1 overexpression mutant showed a reduction in seed productivity compared to the wild type, and particularly, the #17-1 line, in which the AtSPF1 gene was expressed at the highest level, showed a reduction in seed productivity of about 30%. Also, in the mutants in which the expression of the AtSPF1 was inhibited, a reduction in seed productivity compared to the wild type could be observed, even though the degree of the reduction was not great compared to the #17-1 line which showed phenotypes such as a change in chlorophyll concentration.

Also, the seed productivity of mutants other than the selected knockout mutants was examined, and as a result, the seed productivity showed a tendency to decrease compared to that of the wild type. Meanwhile, because the number of seeds formed per pod was maintained at a level similar to that of the wild type, this reduction in seed productivity was considered to be attributable to the reduction in the number of pods formed per individual. However, the reduction in the seed productivity of the AtSPF1 overexpression mutant #17-1 was shown by not only the reduction in the number of pods, but also the reduction in the number of seeds formed per pod.

TABLE 2

| Line | Number of pods | Number of seeds per pod | Total number of seeds | Ratio (%) |
|---|---|---|---|---|
| Wild type | 306.14 ± 122.49 | 44.91 ± 8.45 | 13748.88 ± 382.51 | 100 |
| AtSPF1 K/O | 260.09 ± 36.95 | 44 ± 7.21 | 11444 ± 184.11 | 83.24 |
| Wild type | 48 ± 8.61 | 44.91 ± 8.45 | 2230.24 ± 382.51 | 100 |

TABLE 2-continued

| Line | Number of pods | Number of seeds per pod | Total number of seeds | Ratio (%) |
|---|---|---|---|---|
| AtSPF1 O/E #9-8 | 45.75 ± 11.61 | 44.59 ± 7.42 | 2103.05 ± 581.11 | 94.30 |
| AtSPF1 O/E #17-1 | 37.38 ± 13.47 | 40.60 ± 7.41 | 1572.05 ± 666.83 | 70.49 |

Example 4

Change in Physiological Activity of AtSPF3 Mutants

<4-1> Comparison of Phenotype Between Mutants and Wild Type

The AtSPF3 gene knockout mutants and overexpression mutants together with the wild type were planted in the same pot and grown for 3-5 weeks. Then, the phenotypes of the mutants and the wild type were compared.

Figure 9:
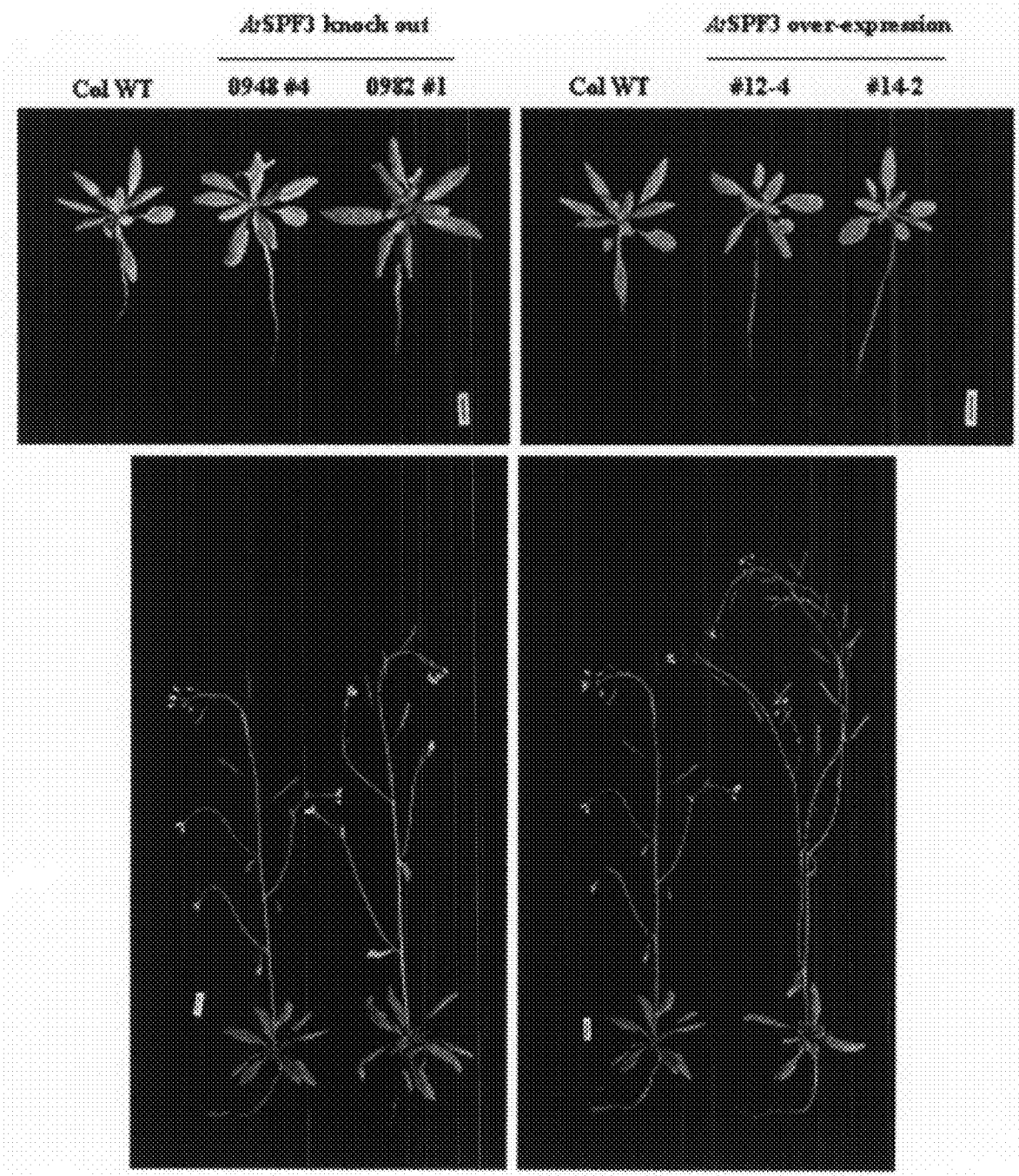
FIG. 9 shows the comparison of phenotypes between the inventive AtSPF3 mutants and the wild type.

As a result, as shown in FIG. 9, in the case of the mutants increased expression of the AtSPF3 gene, the height of the plants was slightly increased compared to that of the wild type, but the morphological change of the leaves or flowers of the transformants could not be observed.

<4-2> Comparison of Life Cycle Between Mutants and Wild Type

The wild type and the AtSPF1 knockout and overexpression mutants were planted and grown in the same pot in order to maintain conditions required for the growth of the plants at the same conditions, and each individual was observed for germination, emergence, bolting, senescence initiation, and 50% senescence. The observation was repeated three times in a batch of two pots.

Figure 10:
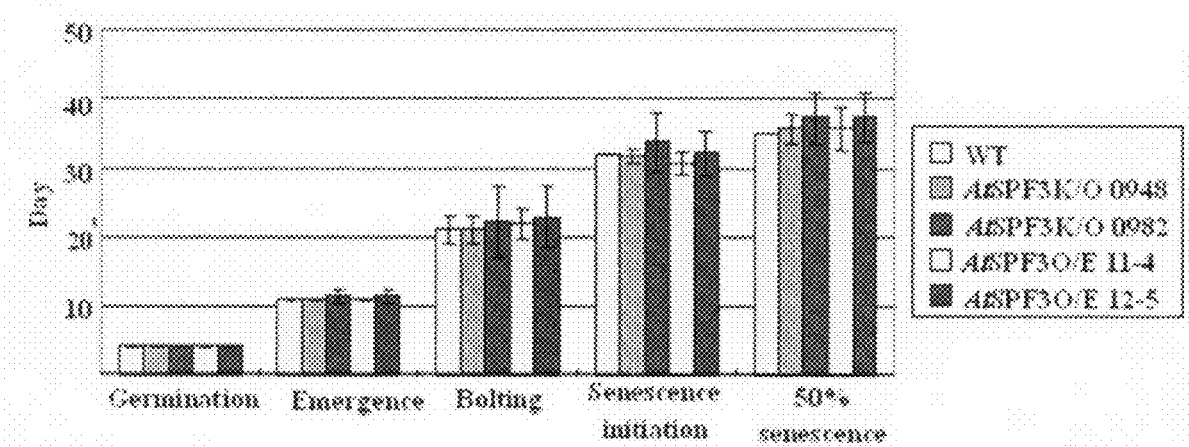
FIG. 10 shows the comparison of life cycles between the inventive AtSPF3 mutants and the wild type.

As a result, as shown in FIG. 10, the general development and life cycle of the transformants were not different from those of the wild type.

<4-3> Change in Hypocotyl Growth Rate

In order to examine the influence of the AtSPF3 gene on the growth of plants, the length of hypocotyls was measured. For this purpose, the transformant seeds, together with the wild type seeds, were sown in 0.5×MS media (containing each of 0%, 1%, 3% and 5% sucrose) and subjected to light treatment for 12 hours. Also, in order to exclude the influence of sugars photosynthesized in seed leaves upon germination, the seeds were subjected to dark treatment for 3.5 days to induce germination. After completion of the dark treatment, the length of the plants, other than the seed leaves and the roots, was measured. The transformant seeds and the wild type seeds were sown at a density of 30 seeds per medium, and the experiment was repeated two times or more in a set of three media.

Figure 11:
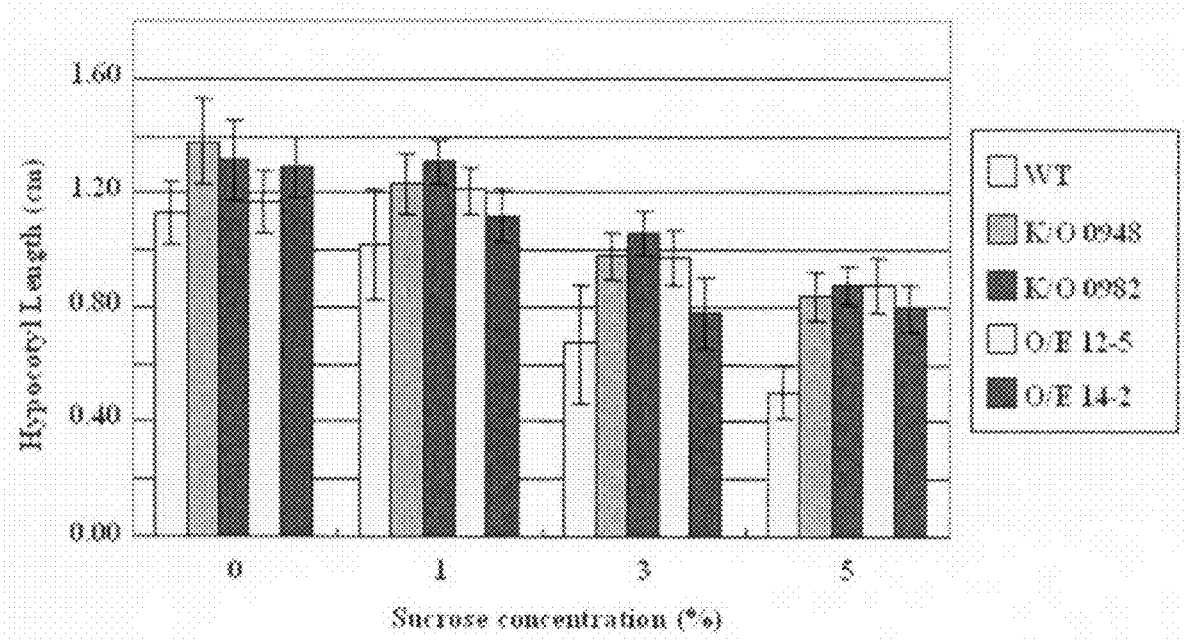
FIG. 11 shows the comparison of hypocotyl growth rates between the inventive AtSPF3 mutants and the wild type in presence of some sucrose concentration.

As a result, as shown in FIG. 11, the hypocotyl length of the transformants was longer than that of the wild type, regardless of the concentration of sucrose or the expression level of the gene, like Example <3-4>.

<4-4> Change in Germination Rate

During the process of measuring the length of hypocotyls in order to examine the association with the plant growth, it could be observed that the germination rate of the transformants was higher than that of the wild type. Thus, in order to examine the influence of treatment with various stresses, including sugars, on the germination rate of the transformants, the following experiment was carried out.

The transformants of the respective genes, together with the wild type, were sown in 0.5×MS media (containing each of 0, 50, 100 and 200 mM NaCl, each of 0, 0.1, 0.5, 1, 5 and 10 µM ABA, each of 0, 1, 3 and 5% sucrose and each of 0, 1, 3, 5, 7 and 10% mannitol) and subjected to light treatment at 23±1° C. for 12 hours and dark treatment for 3.5 days. When the seed leaves were formed, the germination rate of the plants was measured. The transformant seeds and the wild type seeds were sown at a density of 30 seeds per medium, and the experiment was repeated two times or more in a set of three media.

Figure 12:
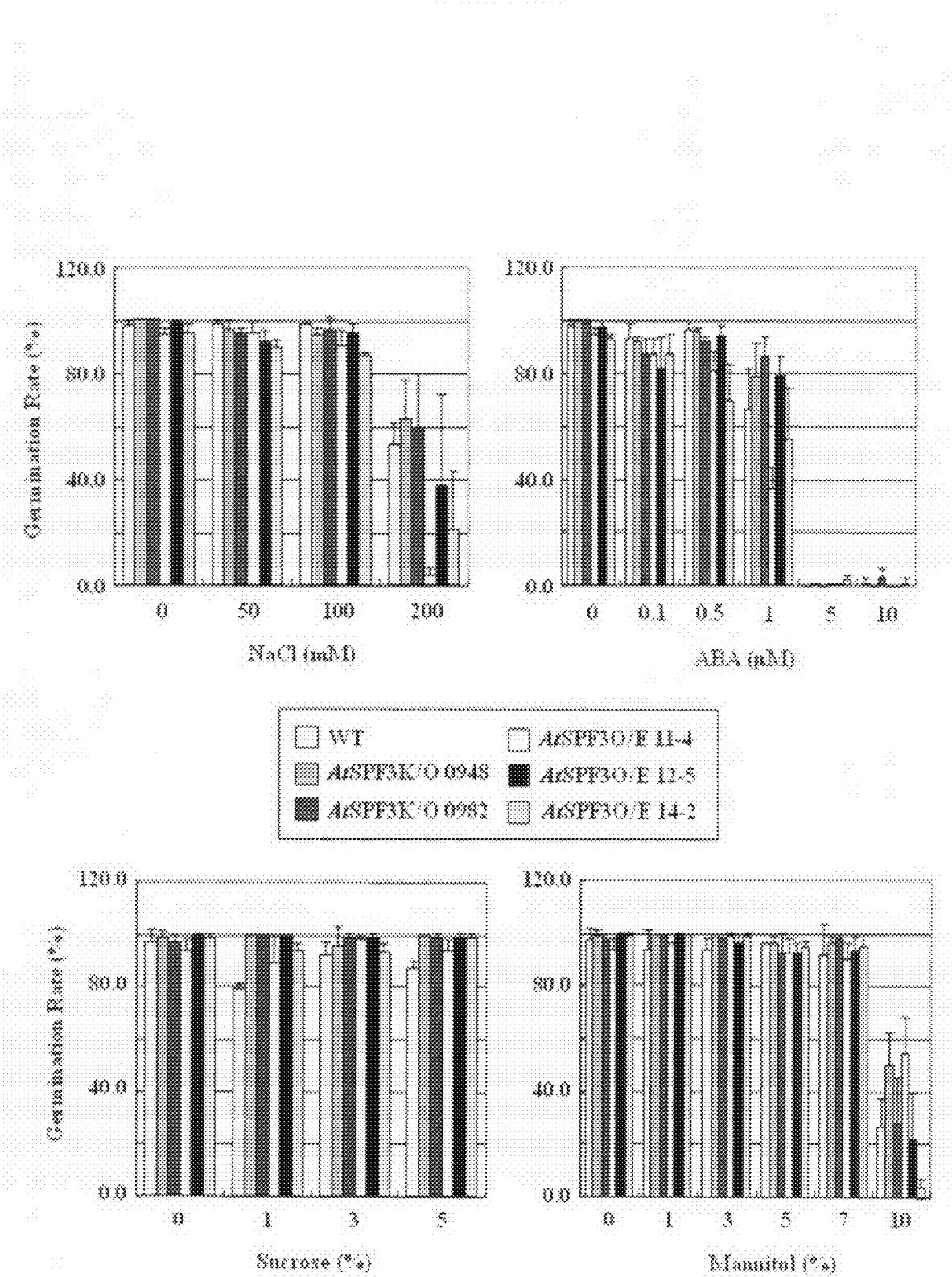
FIG. 12 shows the comparison of germination rates between the inventive AtSPF3 mutants and the wild type under the various kinds of water stress.

As a result, as shown in FIG. 12, the AtSPF3 gene transformants showed a germination rate slightly higher than that of the wild type in treatment with a high concentration of sucrose, but the change in germination rate with the change in the expression level of the gene could not be observed. In treatment with mannitol or the ABA hormone, the knockout mutant and the overexpression mutant did not show a common tendency, but in treatment with salt stress (NaCl), the germination of seeds in the overexpression mutant was inhibited.

<4-5> Change in Seed Productivity

In the AtSPF3 overexpression mutant, the height of plants was increased, and the production of side branches was increased while the number of flowers was increased. Thus, in order to examine the influence of these changes on seed productivity, the seed productivity of each transformant was measured.

The transformant of each gene and the wild type were sown in the same pot and grown at 23±1° C. for 2 months under a long-day condition. The number of pods formed per individual in 10 individuals for each of the transformants and the wild type was recorded, 10 pods per individual were random selected, and the number of seeds produced per pod was recorded. On the basis of the recorded values, the seed productivity was calculated. The experiment was repeated 3 times in a batch of two pots.

As a result, as shown in Table 3 below, the AtSPF3 overexpression mutants showed an increase in seed productivity of about 30% compared to that of the wild type. This was considered to be attributable to an increase in the number of pods formed in the plant, and there was no great difference in the number of seeds formed per pod.

TABLE 3

| Line | Number of pods | Number of seeds per pod | Total number of seeds | Ratio (%) |
|---|---|---|---|---|
| Wild type | 327.92 ± 44.20 | 44.68 ± 7.48 | 14651.6 ± 681.36 | 100 |
| AtSPF3 K/O 0948 | 364.64 ± 43.54 | 43.04 ± 5.72 | 15694.11 ± 684.58 | 107.12 |
| AtSPF3 K/O 0982 | 303.35 ± 36.15 | 44.21 ± 7.60 | 13410.93 ± 1338.23 | 91.53 |

TABLE 3-continued

| Line | Number of pods | Number of seeds per pod | Total number of seeds | Ratio (%) |
| --- | --- | --- | --- | --- |
| Wild type | 45 ± 10.92 | 44.68 ± 7.48 | 2034.98 ± 681.36 | 100 |
| AtSPF3 O/E #12-5 | 64.38 ± 15.15 | 46.90 ± 8.06 | 3038.49 ± 805.45 | 149.31 |
| AtSPF3 O/E #14-2 | 57.14 ± 20.05 | 45.57 ± 6.59 | 2654 ± 1030.35 | 130.49 |

What is claimed is:

1. A method for changing seed productivity of a plant, comprising increasing the intracellular level of an isolated polypeptide having the amino acid sequence consisting of SEQ ID NO: 1, and selecting a plant having increased seed productivity compared to a control plant.

2. The method according to claim 1, wherein the increasing intracellular level is carried out by increasing the expression of a polynucleotide encoding the polypeptide.

3. The method according to claim 2, wherein the polynucleotide has the nucleotide sequence consisting of SEQ ID NO:2.

4. The method according to claim 1, wherein the plant is selected from the group of angiosperm plants consisting of arabidopsis, chinese cabbage, cabbage, mustard, rape, radish, *Brassica napobrassica*, *Brassica rapa/Brassica campestris*, triticale, cauliflower, broccoli, shepherd's purse, *Cardamine flexuosa*, *Arabis glabra*, whitlow grass, *Brassica juncea*, *Brassica napus*, *Brassica oleracea*, *Brassica caulorapa*, *Brassica fimbriata*, *Brassica ruvo*, *Brassica septiceps*, *Brassica nigra*, *Cochlearia officinalis*, *Armoracia lapathifolia*, *Descurainia pinnata* and *Aubrieta deltoidea*.

5. A method for producing a plant having increased seed productivity, comprising the step of transforming a plant with a polynucleotide encoding a polypeptide having the amino acid sequence consisting of SEQ ID NO: 1, and selecting a plant having increased seed productivity compared to a control plant.

6. The method according to claim 5, wherein the polynucleotide has the nucleotide sequence consisting of SEQ ID NO: 2.

* * * * *